(12) United States Patent
Carter et al.

(10) Patent No.: US 11,850,440 B2
(45) Date of Patent: Dec. 26, 2023

(54) THERAPEUTIC SYSTEMS USING MAGNETIC FIELDS

(71) Applicant: University of Iowa Research Foundation, Iowa City, IA (US)

(72) Inventors: Calvin S. Carter, Iowa City, IA (US); Sunny C. Huang, Iowa City, IA (US); Michael J. Miller, Iowa City, IA (US); Charles C. Searby, Iowa City, IA (US); Val C. Sheffield, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 298 days.

(21) Appl. No.: 16/947,824

(22) Filed: Aug. 19, 2020

(65) Prior Publication Data

US 2021/0052910 A1    Feb. 25, 2021

Related U.S. Application Data

(60) Provisional application No. 62/890,372, filed on Aug. 22, 2019.

(51) Int. Cl.
| | | |
|---|---|---|
| *A61N 2/00* | (2006.01) | |
| *A61N 2/02* | (2006.01) | |
| *A61N 2/06* | (2006.01) | |

(52) U.S. Cl.
CPC .............. *A61N 2/004* (2013.01); *A61N 2/02* (2013.01); *A61N 2/06* (2013.01)

(58) Field of Classification Search
CPC ... A61N 2/00; A61N 2/02; A61N 2/06; A61N 2/12; A61N 2/002; A61N 2/006
See application file for complete search history.

(56) References Cited

U.S. PATENT DOCUMENTS

| 3,915,151 A | 10/1975 | Kraus |
|---|---|---|
| 4,428,366 A | 1/1984 | Findl et al. |

(Continued)

FOREIGN PATENT DOCUMENTS

| EP | 1091786 B1 | 12/2005 |
|---|---|---|
| WO | WO-02/098501 A2 | 12/2002 |

(Continued)

OTHER PUBLICATIONS

"U.S. Appl. No. 16/280,551, Non-Final Office Action dated Dec. 11, 2020", 16 pgs.

(Continued)

*Primary Examiner* — Samuel G Gilbert
(74) *Attorney, Agent, or Firm* — Schwegman Lundberg & Woessner, P.A.

(57) ABSTRACT

A system may include one, two or more magnetic field systems. The magnetic field system may be configured to provide a magnetic field in a first direction to the tissue. The magnetic field system may include at least one magnetic field source to produce the magnetic field. The magnetic field produced by the at least one magnetic field source may include a magnetic field produced by at least one of a permanent magnet, a temporary magnet or electric current flow through a conductor. The same or a second magnetic field system may be configured to provide a second magnetic field in a second direction to the tissue. The magnetic field system may include two or more sources to provide the magnetic field in a second, third or fourth direction that is non-parallel to the first direction.

8 Claims, 21 Drawing Sheets

(56) References Cited

U.S. PATENT DOCUMENTS

| | | | |
|---|---|---|---|
| 4,556,051 A | | 12/1985 | Maurer |
| 4,838,850 A | * | 6/1989 | Rosengart ............. A61N 2/002 600/14 |
| 4,850,959 A | | 7/1989 | Findl |
| 5,267,152 A | | 11/1993 | Yang et al. |
| 5,267,252 A | | 11/1993 | Amano |
| 5,803,896 A | | 9/1998 | Chen |
| 6,048,302 A | * | 4/2000 | Markoll ............... A61N 2/02 600/13 |
| 6,210,317 B1 | | 4/2001 | Bonlie |
| 6,418,345 B1 | * | 7/2002 | Tepper .................. A61N 2/02 607/51 |
| 6,443,883 B1 | * | 9/2002 | Ostrow ................ A61N 2/008 600/14 |
| 6,652,444 B1 | | 11/2003 | Ross |
| 6,751,506 B2 | | 6/2004 | Shealy |
| 6,856,839 B2 | | 2/2005 | Litovitz |
| 8,700,161 B2 | | 4/2014 | Harel et al. |
| 8,825,174 B2 | | 9/2014 | Panting |
| 9,320,913 B2 | | 4/2016 | Dimino et al. |
| 9,327,136 B2 | | 5/2016 | Hedgecock |
| 2001/0044643 A1 | | 11/2001 | Litovitz |
| 2002/0198567 A1 | | 12/2002 | Keisari et al. |
| 2003/0055464 A1 | | 3/2003 | Darvish et al. |
| 2004/0176805 A1 | | 9/2004 | Whelan et al. |
| 2005/0197522 A1 | * | 9/2005 | Pilla .................... A61N 2/008 600/13 |
| 2005/0215842 A1 | | 9/2005 | Pilla et al. |
| 2005/0267535 A1 | | 12/2005 | Tofani |
| 2006/0167499 A1 | | 7/2006 | Palti |
| 2007/0173889 A1 | | 7/2007 | Rosenspire et al. |
| 2008/0057556 A1 | | 3/2008 | Miyakoshi et al. |
| 2008/0087288 A1 | | 4/2008 | Wun |
| 2009/0131993 A1 | | 5/2009 | Rousso et al. |
| 2010/0197993 A1 | | 8/2010 | Vasishta |
| 2011/0105828 A1 | * | 5/2011 | Perless .................. A61N 2/06 600/15 |
| 2011/0230939 A1 | | 9/2011 | Weinstock |
| 2012/0302821 A1 | | 11/2012 | Burnett |
| 2013/0178910 A1 | | 7/2013 | Azamian et al. |
| 2014/0194668 A1 | | 7/2014 | Hanson |
| 2014/0296948 A1 | | 10/2014 | Sluijter |
| 2014/0357935 A1 | * | 12/2014 | Ilmoniemi ............ A61N 2/006 600/13 |
| 2016/0129273 A1 | * | 5/2016 | Park .................... A61N 1/0456 607/3 |
| 2018/0221656 A1 | | 8/2018 | Garcia Perez et al. |
| 2019/0126036 A1 | | 5/2019 | Franco-obregon et al. |
| 2019/0255344 A1 | | 8/2019 | Carter et al. |
| 2021/0272664 A1 | | 9/2021 | Carter et al. |

FOREIGN PATENT DOCUMENTS

| | | |
|---|---|---|
| WO | WO-2008/019710 A1 | 2/2008 |
| WO | WO-2009/061142 A2 | 5/2009 |
| WO | WO-2009/090440 A1 | 7/2009 |
| WO | WO-2010/067180 A2 | 6/2010 |
| WO | WO-2012/083259 A2 | 6/2012 |
| WO | WO-2014/070287 A1 | 5/2014 |
| WO | WO-2015/069446 A1 | 5/2015 |
| WO | WO-2019/164903 A1 | 8/2019 |

OTHER PUBLICATIONS

"U.S. Appl. No. 16/280,551, Notice of Allowance dated Mar. 24, 2021", 11 pgs.

"U.S. Appl. No. 16/280,551, Response filed Mar. 11, 2021 to Non-Final Office Action dated Dec. 11, 2020", 10 pgs.

"Australian Application Serial No. 2019223992, First Examination Report dated Mar. 6, 2021", 6 pgs.

"Effect of Intensive Therapy on Residual B-Cell Function in Patients with Type 1 Diabetes in the Diabetes Control and Complications Trial—A Randomized, Controlled Trial", Annals of Internal Medicine, 128(7), (1998), 517-523.

"European Application Serial No. 19709259.6, Response filed Mar. 23, 2021 to Communication pursuant to Rules 161(2) and 162 EPC", 30 pgs.

"Far Infrared Radiation Treatment for Diabetes", [online]. Retrieved from the Internet: <URL: https://clinicaltrials.gov/ct2/show/NCT00573456>, (Aug. 2009), 5 pgs.

"Guidance for Industry—Diabetes Mellitus: Developing Drugs and Therapeutic Biologics for Treatment and Prevention", U. S. Department of Health and Human Services, Food and Drug Administration, (Feb. 2008), 34 pgs.

"International Application Serial No. PCT/US2019/018716, International Preliminary Report on Patentability dated Sep. 3, 2020", 9 pgs.

"International Application Serial No. PCT/US2019/018716, International Search Report dated Jun. 6, 2019", 6 pgs.

"International Application Serial No. PCT/US2019/018716, Written Opinion dated Jun. 6, 2019", 9 pgs.

Ahmad, Waqar, et al., "Oxidative toxicity in diabetes and Alzheimer's disease: mechanisms behind ROS/RNS generation", Journal of Biomedical Science, 24: 76, (2017), 1-10.

Alfaras, Irene, et al., "Health benefits of late-onset metformin treatment every other week in mice", npj Aging and Mechanisms of Disease, 3: 16, (2017), 1-13.

Barber, Sian, et al., "Oxidative stress in ALS: Key role in motor neuron injury and therapeutic target", Free Radical Biology & Medicine, 48, (2010), 629-641.

Birch-Machin, Mark A., et al., "An Evaluation of the Measurement of the Activities of Complexes I-IV in the Respiratory Chain of Human Skeletal Muscle Mitochondria", Biochemical Medicine and Metabolic Biology, 51, (1994), 35-42.

Blaser, Heiko, et al., "TNF and ROS Crosstalk in In?ammation", Trends in Cell Biology, 26(4), (Apr. 2016), 249-261.

Bouzid, Mohamed A., et al., "Radical Oxygen Species, Exercise and Aging: An Update", Sports Med, 45, (2015), 1245-1261.

Buckingham, Bruce, et al., "Effectiveness of Early Intensive Therapy on B-Cell Preservation in Tpe 1 Diabetes", Diabetes Care. published online Oct. 15, 2013, (2013), 1-6.

Caduff, A., et al., "First human experiments with a novel non-invasive, non-optical continuous glucose monitoring system", Biosensors & Bioelectronics, 19(3), (2003), 209-217.

Carter, Calvin S., et al., "Abnormal development of NG2+PDGFR-a+ neural progenitor cells leads to neonatal hydrocephalus in a ciliopathy mouse model", Nature Medicine, 18(12), (2012), 1797-1804 (9 pgs.).

Cox, Carly S., et al., "Mitohormesis in Mice via Sustained Basal Activation of Mitochondrial and Antioxidant Signaling", Cell Metab., 28(5), (2018), 776-786.

Curry, Daniel W., et al., "Targeting AMPK Signaling as a Neuroprotective Strategy in Parkinson's Disease", Journal of Parkinson's Disease, 8, (2018), 161-181.

De Haes, Wouter, et al., "Metformin promotes lifespan through mitohormesis via the peroxiredoxin PRDX-2", Proc. of the Natl. Acad. Sci. USA, 111, (2014), E2501-E2509.

Devos, David, et al., "Targeting Chelatable Iron as a Therapeutic Modality in Parkinson's Disease", Antioxidants & Redox Signaling, 21(2), (2014), 195-210.

Dugan, Laura L., et al., "AMPK dysregulation promotes diabetes-related reduction of superoxide and mitochondrial function", The Journal of Clinical Investigation, vol. 123, No. 11, (Nov. 2013), 4888-4899.

El-Kenawi, Asmaa, et al., "Inflammation, ROS, and Mutagenesis", Cancer Cell, 32, (2017), 727-729.

Finkel, Toren, "Signal transduction by reactive oxygen species", J. Cell Biol., 194(1), (2011), 7-15.

Fisher-Wellman, Kelsey H., et al., "Linking mitochondrial bioenergetics to insulin resistance via redox biology", Trends in Endocrinology and Metabolism, 23(3), (Mar. 2012), 142-153.

Foretz, Marc, et al., "Metformin inhibits hepatic gluconeogenesis in mice independently of the LKB1/AMPK pathway via a decrease in hepatic energy state", The Journal of Clinical Investigation, 120(7), (Jul. 2010), 2355-2369.

(56) References Cited

OTHER PUBLICATIONS

Furman, Brian L., et al., "Streptozotocin-Induced Diabetic Models in Mice and Rats", Curr. Protoc. Pharmacol., Suppl. 70, (Sep. 2015), 5.47.1-5.47.20.
Glasauer, Andrea, et al., "Targeting antioxidants for cancer therapy", Biochemical Pharmacology, 92, (2014), 90-101.
Havas, Magda, "Dirty Electricity Elevates Blood Sugar Among Electrically Sensitive Diabetics and May Explain Brittle Diabetes", Electromagnetic Biology and Medicine, 27, (2008), 135-146.
Hwang, Onyou, et al., "Role of Oxidative Stress in Parkinson's Disease", Experimental Neurobiology, 22(1), (2013), 11-17.
Jin, Huajun, et al., "Mitochondria-Targeted Antioxidants for Treatment of Parkinson's Disease: Preclinical and Clinical Outcomes", NIH Public Access, Author manuscript, published in final edited form as: Biochim Biophys Acta., 1842(8), (2014), 1282-1294, (2014), 33 pgs.
Keymeulen, B., et al., "Four-year metabolic outcome of a randomised controlled CD3-antibody trial in recent-onset type 1 diabetic patients depends on their age and baseline residual beta cell mass", Diabetologia, 53, (2010), 614-623.
King, Aileen J. F., et al., "The use of animal models in diabetes research", British Journal of Pharmacology, 166, (2012), 877-894.
Kirillov, I. B., et al., "[Magentotherapy in the comprehensive treatment of vascular complications of diabetes mellitus]", Klin Med (Mosk), 74(5), (1996), 39-41, (1996), 1 pg.
Kobayashi, Kunihisa, et al., "The db/db Mouse, a Model for Diabetic Dyslipidemia: Molecular Characterization and Effects of Western Diet Feeding", Metabolism, 49(1), (2000), 22-31.
Kumar, Anil, et al., "A review on mitochondrial restorative mechanism of antioxidants in Alzheimer's disease and other neurological condictions", Frontiers in Pharmacology, vol. 6, Article 206, (Sep. 2015), 1-13.
Lark, D. S., et al., "Enhanced Mitochondrial Superoxide Scavenging Does Not Improve Muscle Insulin Action in the High Fat-Fed Mouse", Plos One 10(5): e0126732, (2015), 1-11.
Lee, Sihoon, et al., "Comparison between surrogate indexes of insulin sensitivity and resistance and hyperinsulinemic euglycemic clamp estimates in mice", Am J Physiol Endocrinol Metab, 294, (2008), E261-E270.
Leloup, Corinne, et al., "Mitochondrial Reactive Oxygen Species Are Obligatory Signals for Glucose-Induced Insulin Secretion", Diabetes, vol. 58, (Mar. 2009), 673-681.
Liochev, Stefan I., et al., "Reactive oxygen species and the free radical theory of aging", Free Radical Biology and Medicine, 60, (2013), 1-4.
Livingstone, Shona J., et al., "Estimated Life Expectancy in a Scottish Cohort With Type 1 Diabetes, 2008-2010", JAMA, 313(1), (2015), 37-44.
Loh, Kim, et al., "Reactive Oxygen Species Enhances Insulin Sensitivity", Cell Metabolism, 10, (2009), 260-272.
Luna-Lopez, Armando, et al., "New considerations on hormetic response against oxidative stress", J. Cell Commun. Signal, 8(4), (2014), 323-331.
Madiraju, Anila K., et al., "Metformin suppresses gluconeogenesis by inhibiting mitochondrial glycerophosphate dehydrogenase", Nature, 510, (2014), 542-546 (17 pgs.).
Mahadev, Kalyankar, et al., "The NAD(P)H Oxidase Homolog Nox4 Modulates Insulin-Stimulated Generation of H2O2 and Plays an Integral Role in Insulin Signal Transduction", Molecular and Cellular Biology, 24(5), (Mar. 2004), 1844-1854.
Markesbery, William R., "The Role of Oxidative Stess in Alzheimer's Disease", Arch Neurol, 56, (1999), 1449-1452.
Martin-Montalvo, Alejandro, et al., "Metformin improves healthspan and lifespan in mice", HHS Public Access, Author manuscript, published in final edited form as: Nat Commun., 4, (2013), 2192, (2013), 23 pgs.

Mittal, Manish, et al., "Reactive Oxygen Species in Inflammation and Tissue Injury", Antioxidants & Redox Signaling, 20(7), (2014), 1126-1167.
Mogavero, Angelo, et al., "Metformin transiently inhibits colorectal cancer cell proliferation as a result of either AMPK activation or increased ROS production", Scientific Reports, 7: 15992, (2017), 1-12.
Owen, Mark R., et al., "Evidence that metformin exerts its antidiabetic effects through inhibition of complex 1 of the mitochondrial respiratory chain", Biochem. J., 348, (2000), 607-614.
Pearce, O. M., et al., "Hormesis in cancer immunology: Does the quantity of an immune reactant matter", Oncoimmunology, 3, e29312, 3 pgs.
Poprac, Patrik, et al., "Targeting Free Radicals in Oxidative Stress-Related Human Diseases", Trends in Pharmacological Sciences, 38(7), (Jul. 2017), 592-607.
Puspita, Lesly, et al., "Oxidative stress and cellular pathologies in Parkinson's disease", Molecular Brain, 10: 53, (2017), 12 pgs.
Qinna, Nidal A., et al., "Impact of streptozotocin on altering normal glucose homeostasis during insulin testing in diabetic rats compared to normoglycemic rats", Drug Design, Development and Therapy, 9, (2015), 2515-2525.
Radak, Zsolt, et al., "Exercise and hormesis: oxidative stress-related adaptation for successful aging", Biogerontology, 6, (2005), 71-75.
Raza, Muhammad H., et al., "ROS-modulated therapeutic approaches in cancer treatment", J. Cancer Res Clin Oncol, 143, (2017), 1789-1809.
Sherifali, Diana, et al., "The Effect of Oral Antidiabetic Agents on Glycated Hemoglobin Levels: A Systematic Review and Meta-Analysis", Diabetes Care, (2010), 1-11.
Sieron, A., "Effect of Low Frequency Electromagnetic Fields on [3H]Glucose Uptake in Rat Tissues", Polish J. of Environ. Stud., 16(2), (2007), 309-312.
Simm, Andreas, et al., "Reactive oxygen species (ROS) and aging: Do we need them can we measure them should we block them?", Signal Transduction, 3, (2005), 115-125.
Song, Chang W., et al., "Metformin kills and radiosensitizes cancer cells and preferentially kills cancer stem cells", Scientific Reports, 2: 362, (2012), 1-9.
Steffes, Michael W., et al., "B-Cell Function and the Development of Diabetes-Related Complications in the Diabetes Control and Complications Trial", Diabetes Care, 26(3), (Mar. 2003), 832-836.
Tonnies, Eric, et al., "Oxidative Stress, Synaptic Dysfunction, and Alzheimer's Disease", Journal of Alzheimer's Disease, 57, (2017), 1105-1121.
Valencia, Willy M., et al., "Metformin and ageing: improving ageing outcomes beyond glycaemic control", HHS Public Access, Author manuscript, published in final edited form as: Diabetologia, 60(9), (2017), 1630-1638, (2017), 16 pgs.
Vetere, Amedeo, et al., "Targeting the pancreatic ß-cell to treat diabetes", Nature Reviews Drug Discovery, 13, (Aceil 2014), 278-289.
Wang, G, J., et al., "Low-dose radiation and its clinical implications: diabetes", Hum Exp Toxicol, 27(2), (2008), 135-142.
Wang, Huizhen, et al., "Magnetic Fields and Reactive Oxygen Species", Int. J. Mol. Sci., 18, 2175, (2017), 20 pgs.
Wang, Jian, "Mitochondria as a therapeutic target in Alzheimer's disease", Genes & Diseases, 3, (2016), 220-227.
Wheaton, William W., et al., "Metformin inhibits mitochondrial complex I of cancer cells to reduce tumorigenesis", eLife, 3:e02242, (2014), 18 pgs.
Yang, Xiangjun, et al., "Antioxidant Treatment Limits Neuroin? ammation in Experimental Glaucoma", IOVS, 57(4), (Apr. 2016), 2344-2354.
Zhang, Hui-Hui, et al., "Combinational strategies of metformin and chemotherapy in cancers", Cancer Chemother Pharmacol, 78, (2016), 13-26.
U.S. Appl. No. 17/307,830, filed May 4, 2021, Closed-Loop AI-Optimized EMF Treatment and Digital Delivery of Data.

\* cited by examiner

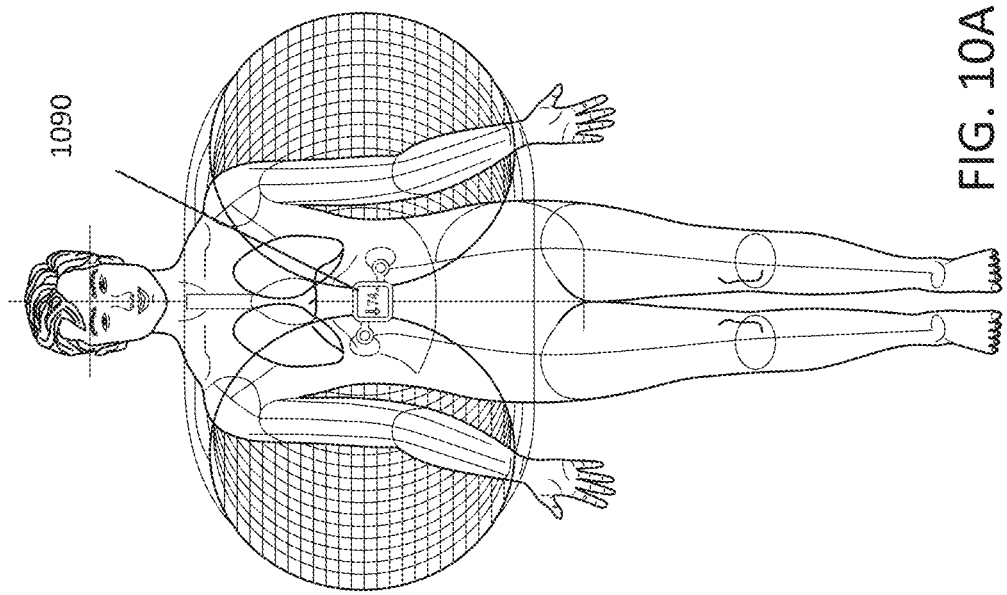
FIG. 10A
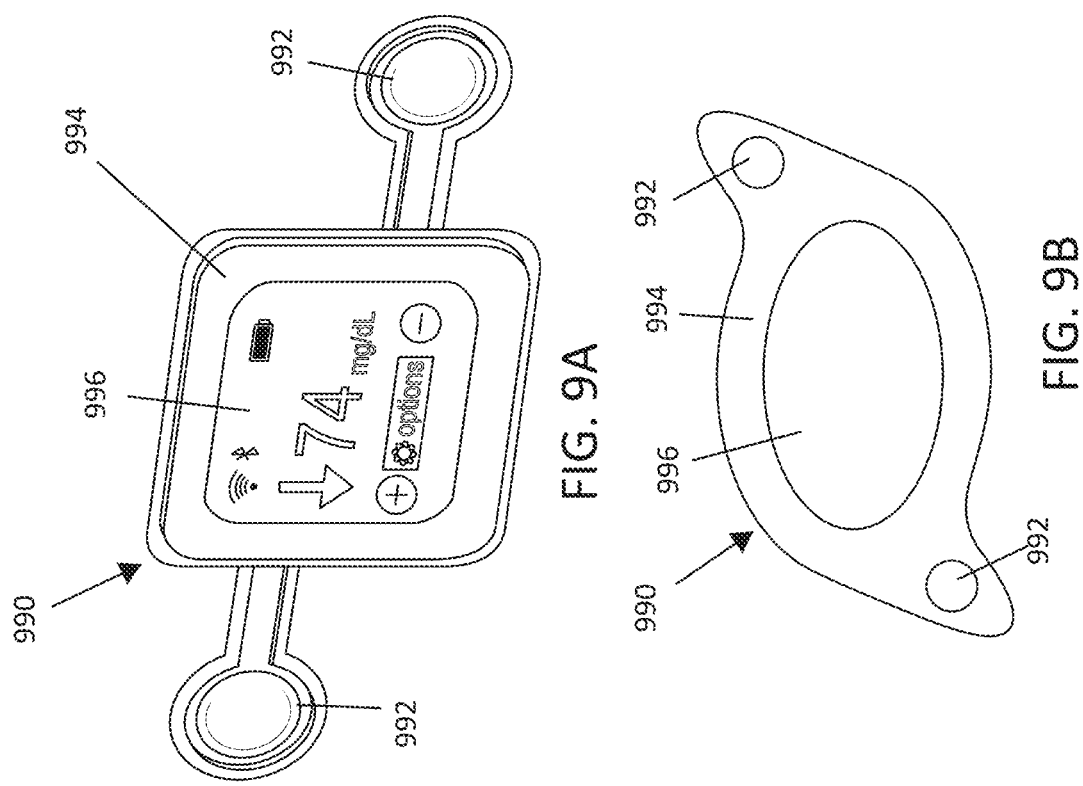
FIG. 9A
FIG. 9B

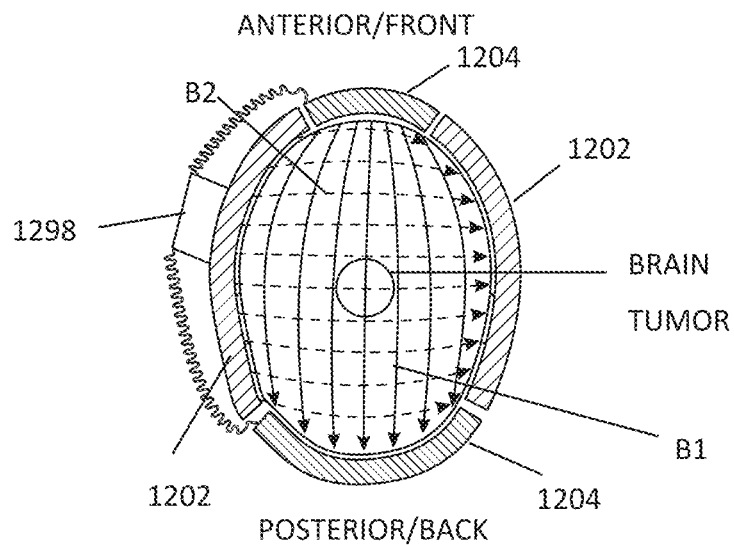
FIG. 12
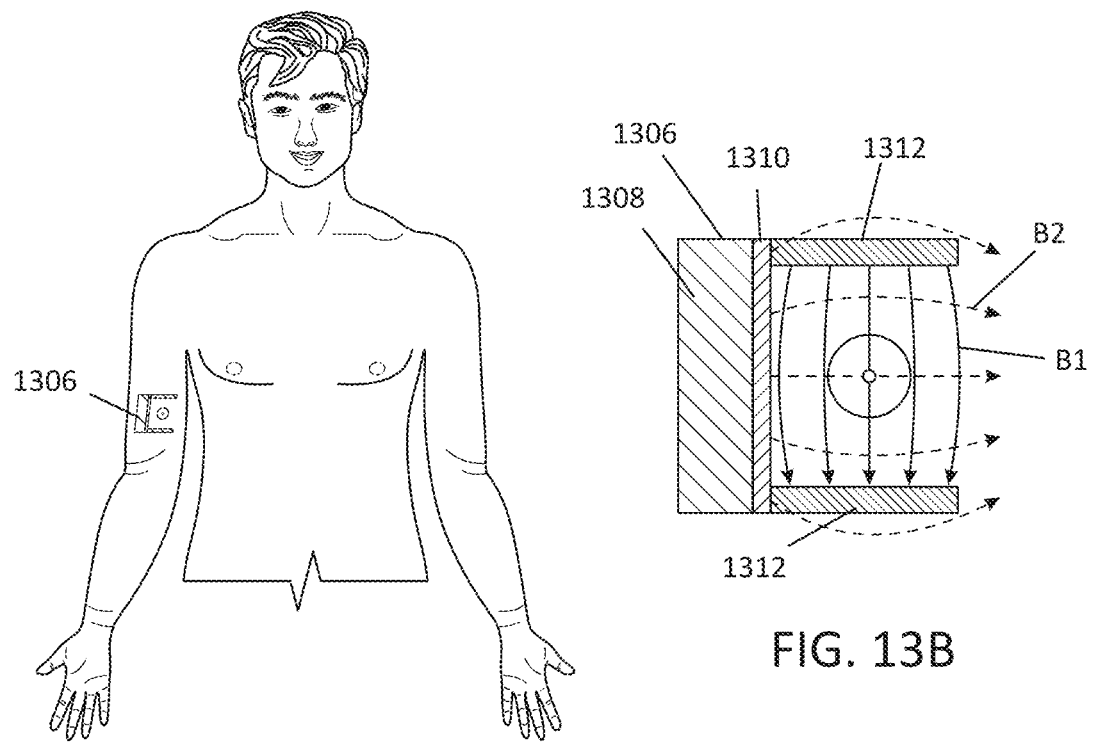
FIG. 13A
FIG. 13B

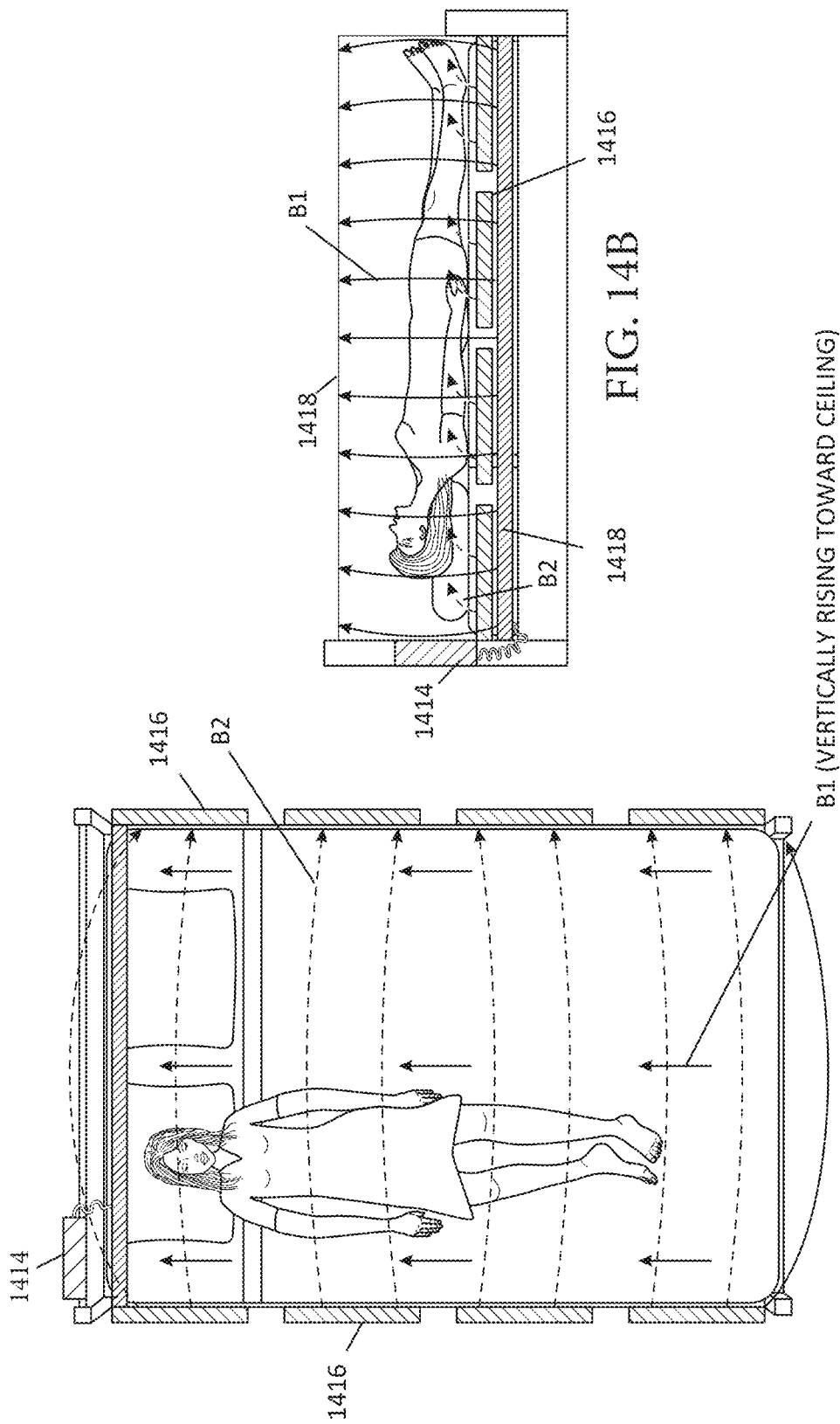

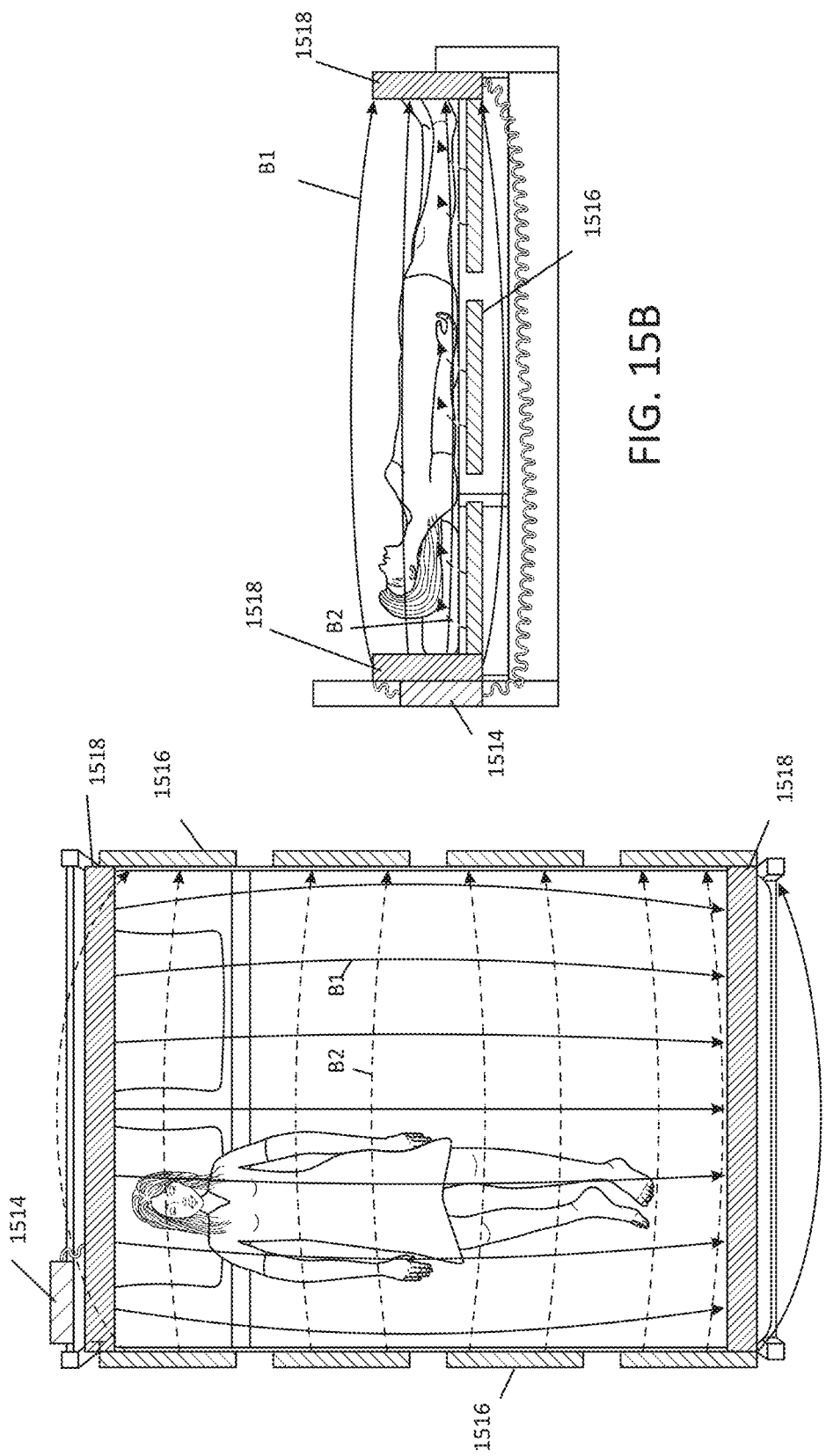

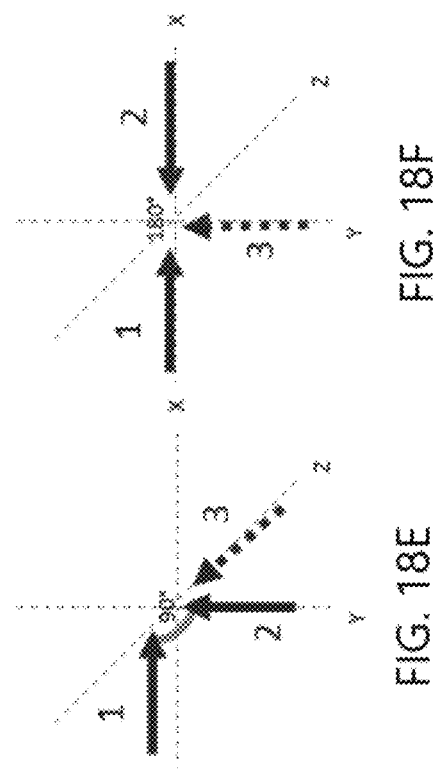
FIG. 18A
FIG. 18B
FIG. 18C
FIG. 18D
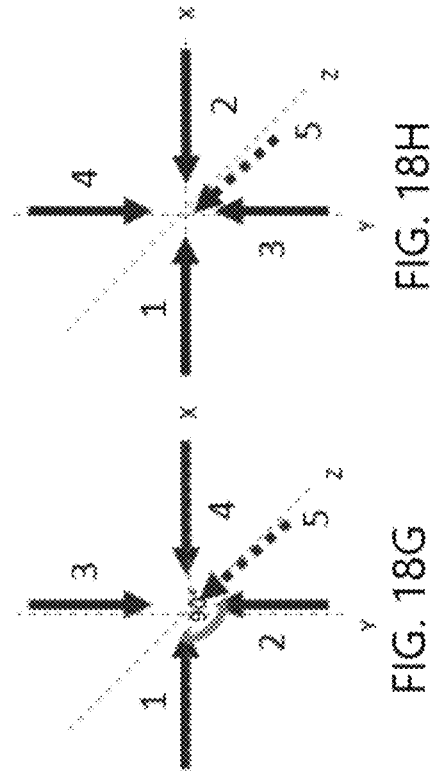
FIG. 18E
FIG. 18F
FIG. 18G
FIG. 18H

THERAPEUTIC SYSTEMS USING MAGNETIC FIELDS

CLAIM OF PRIORITY

This application claims the benefit of priority under 35 U.S.C. § 119(e) of U.S. Provisional Patent Application Ser. No. 62/890,372, filed on Aug. 22, 2019, and titled "THERAPEUTIC SYSTEMS USING MAGNETIC FIELDS", which is incorporated by reference herein in its entirety.

TECHNICAL FIELD

The present disclosure relates generally to medical systems, and more particularly, to systems, devices, and methods for delivering therapy by delivering energy to tissue.

BACKGROUND

Existing therapies for chronic diseases, such as but not limited diabetes, cancer, neurological and immune diseases, have significant challenges. For example, existing therapies may only treat symptoms of the disease, may be invasive, and/or may have relatively low patient adherence. By way of a non-limiting example, many diabetic patients have failed to achieve a healthy glycemic range and have a significantly greater risk of premature death in spite of the medications that are available to manage the disease. Patients may fail to adhere to their therapy because of the complexity of the dosing regimen for their prescribed medication, the discomfort of testing and insulin injections, and drug intolerability. Conventional diabetic care and the cost of treating complications resulting from poorly-managed diabetes is very costly. Many current therapies do not ameliorate redox imbalance, an underlying cause of insulin resistance and type 2 diabetes. Attempts to reverse redox imbalance in T2D using redox-modulating drugs or infusion of antioxidants (e.g. glutathione) have shown promise in reversing insulin resistance in preliminary human studies, but ultimately have failed in clinical trials due to their short half-lives and delivery challenges.

What is needed is an improved therapy for treating chronic diseases that targets the underlying causes of type 2 diabetes and addresses some of these shortcomings of existing therapies.

Modulation of redox systems can be achieved by altering the homeostasis of pro-oxidants including reactive oxygen species (ROS), many of which are paramagnetic.

SUMMARY

This Summary includes examples that provide an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

Various examples described herein may modulate redox systems via interactions with paramagnetic molecules, such as ROS, to ameliorate redox imbalance for the treatment of redox-related disease, including but not limited to diabetes, cancer, neurological disease, inflammatory disease, mental health disorders, addictions and immune related disease etc.

An example (e.g. Example 1) of subject matter (such as a system, a device, apparatus or machine) may deliver a therapy by delivering energy to tissue. The system may comprise one, two or more magnetic field systems. The magnetic field system may be configured to provide a magnetic field in a first direction to the tissue. The magnetic field system may include at least one magnetic field source to produce the magnetic field. The magnetic field produced by the at least one magnetic field source may include a magnetic field produced by at least one of a permanent magnet, a temporary magnet or electric current flow through a conductor. The same or a second magnetic field system may be configured to provide a second magnetic field in a second direction to the tissue. The magnetic field system may include two or more sources to provide the magnetic field in a second, third or fourth direction that is non-parallel to the first direction.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 9A-9B illustrate, by way of example and not limitation, embodiments of a system in the form of a patch-like device.

FIGS. 10A-10B illustrate the patch-like device of FIG. 9A implemented as a wearable device adhered or otherwise attached directly or indirectly to the patient and as an environmental device under the bed mattress, respectively.

FIG. 12 illustrates an embodiment of a wearable MNPMF system as an article to be worn on the head.

FIGS. 13A-B illustrate an embodiment of an implantable MNPMF system, illustrated by way of example and not limitation, around a tumor in an arm.

FIGS. 14A-B illustrate an embodiment of an environmental MNPMF system, illustrated by way of example and not limitation, around a patient's bed.

FIGS. 15A-B illustrate an embodiment of an environmental MNPMF system, illustrated by way of example and not limitation, around a patient's bed.

FIGS. 18A-18H illustrate examples of non-parallel field orientations.

FIGS. 23A and 23B-24A and 24B show that significant reductions, respectively, in liver and circulating (plasma) fatty acids including, MCFA, LCFA, PUFA, fatty acid dicarboxylates, acyl glycines, amino fatty acids, and significant increases in carnitines occur with 3 days of MNPEF treatment in diabetic animal models.

DETAILED DESCRIPTION

Figure 1:
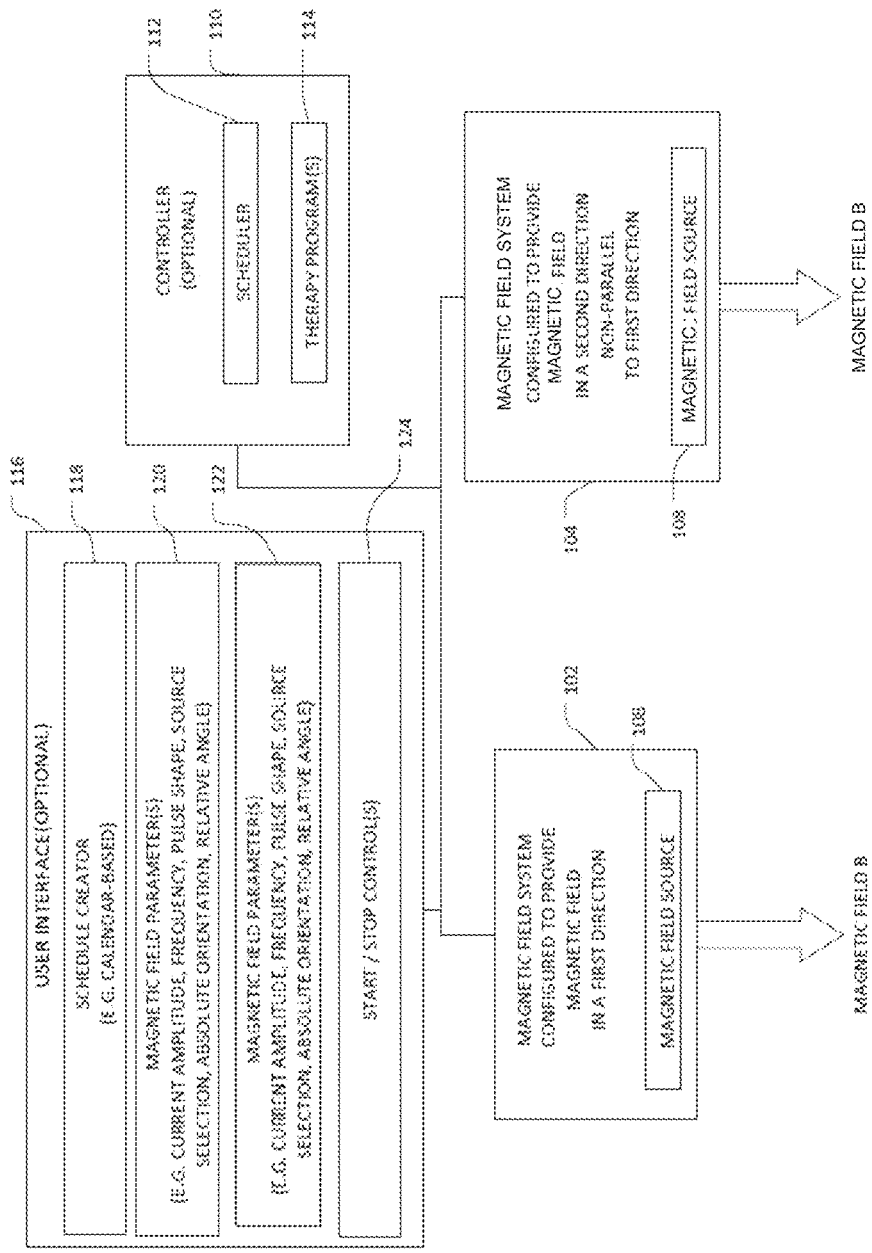
FIG. 1 illustrates, by way of example and not limitation, a system configured to deliver energy (e.g. Magnetic Non-Parallel Magnetic Field or "MNPMF") to tissue as part of a therapy.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This application incorporates by reference, in their entirety, the following applications: U.S. Provisional Patent Application Ser. No. 62/632,540, filed on Feb. 20, 2018, and titled "TREATMENT OF DIABETES USING MAGNETIC AND NON-PARALLEL ELECTROSTATIC FIELDS"; and U.S. patent application Ser. No. 16/280,551, filed on Feb. 20, 2019 and published as U.S. 20190255344 A1, and titled THERAPEUTIC SYSTEMS USING MAGNETIC AND ELECTRIC FIELDS.

Various embodiments of the present subject matter apply two or more DC or AC (out of phase) magnetic fields at non-parallel orientations. Examples of non-parallel orientations include orthogonal (90°) or opposite (180°) orientations. These fields may be applied in a step-wise manner, the first being applied at angle 0 and the second at 90, 180 or angles in between. The time between the end the first field and the beginning of the second field is the pulse rate. By way of example and not limitation, the effective pulse rate may be 0-15 Hz. By way of example and not limitation, the effective duration of each pulse may be 0-5 s, 5-10 s. By way of example and not limitation, the effective magnetic field flux of each pulse may be 3 mT. By way of example and not limitation, the effective range may be between 0-25 mT. Applying two or more magnetic fields in stepwise manner at opposite angles (0-180 and 90 and 270) may be effective for therapies described herein. The present subject matter may be used to treat diseases associated with disrupted metabolism (i.e. type 1 and 2 diabetes, obesity, cancer, Alzheimer's disease, Parkinson's disease, glaucoma, blindness, arthritis, inflammation, auto-immune, infection). The therapy is safe, and may be applied in a non-invasive manner. The therapy may be applied in a passive manner. The therapy may be applied in an automated manner.

FIGS. 18A-18D illustrate some examples of non-parallel magnetic field orientation. Magnetic fields may be applied at 90 (FIG. 18A) or 180 degrees (FIG. 18B) in non-parallel directions with respect to each other. With reference to FIGS. 18C and 18D, fields may be applied in a sequence at non-parallel orientations with respect to one another (1-2-3-4). As illustrated in FIGS. 18E-18H, an electric field may be combined with the non-parallel magnetic field orientation. For example, magnetic fields may be applied at 90 (FIG. 18E) or 180 degrees (FIG. 18F) in non-parallel directions (1, 2) with respect to each other, and a non-parallel electric field may be applied in the Z (orthogonal) direction (3). With reference to FIGS. 18G and 18H, fields may be applied in a sequence at non-parallel orientations with respect to one another (1-2-3-4) along with a non-parallel electric field applied in the Z (orthogonal) direction (5). The electric field may be applied concurrently with the application of the magnetic field in at least one of the magnetic field directions, or may be applied non-concurrently with the magnetic field.

The regulation of metabolism is important for maintaining health. Stressors that cause the metabolic set point to deviate can lead to disease when not sufficiently compensated for. The cell has evolved sophisticated mechanisms to regulate the metabolic set point using redox signaling, which refers to systems that regulate the balance between oxidants and antioxidants. Oxidative stress refers to the deviation away from metabolic steady state (balance of oxidants and antioxidants), toward an oxidized state (more oxidants present than antioxidants). When this occurs, disease ensues. The following diseases are known to be caused by a dysregulation of redox, diabetes mellitus, cancer, metastatic cancer, obesity, inflammation, auto-immune, neurological (Alzheimer's, Parkinson's, ALS), glaucoma, retinitis pigmentosa.

The application of these out of phase, non-parallel fields are currently believed to stabilize reactive oxygen species, reactive nitrogen species and a variety of free radicals. Stabilization of these molecules induces adaptive intracellular changes, including the induction of enzymatic and non-enzymatic anti-oxidant responses, also referred to as "hormesis". These hormetic changes make cells more resilient to oxidative stress. We discovered that oxidants can be stabilized using electromagnetic fields applied at orthogonal orientations. Applying at least two magnetic fields at non-parallel orientations stabilizes oxidants, inducing hormetic changes in cells that lead to upregulation of antioxidant pathways and the amelioration of oxidative stress. These changes create a healthy physiological environment that is therapeutic.

Many diseases are caused by an imbalance of free radicals. Free radicals, including reactive oxygen species (ROS) and reactive nitrogen species (RNS), have been implicated in the pathogenesis of a wide range of chronic diseases. The majority of free radicals are produced in the mitochondria as a result of cellular respiration. Free radicals are also generated in other cellular compartments by various enzymes and biological processes. Although free radicals were once thought to be destructive to the cell, there is a growing body of evidence demonstrating that free radicals act as signaling molecules, transmitting crucial information that contributes to the health state of the cell. The therapy protocol disclosed herein has been shown, through experiment, to increase free radicals (e.g. ROS). It has also been shown, through experiment, that at least some of the therapeutic benefits of the therapy are mediated by free radicals (e.g. ROS). Therefore, the present subject matter is believed to provide an effective therapy for diabetes and cancer, as well as for other diseases and conditions such as but not limited to neurological and immune related disorders (e.g. inflammation), and retinovascular disease. The present subject matter is also believed to provide therapeutic benefits against the aging process.

Hormesis

Free radicals, including reactive oxygen species (ROS) and reactive nitrogen species (RNS) have been implicated in the pathogenesis of a wide range of chronic diseases. The majority of free radicals are produced in the mitochondria as a result of cellular respiration. Free radicals are also generated in other cellular compartments by various enzymes. Free radicals were once thought to be destructive to the cell, however, there is a growing body of evidence demonstrating that free radicals can induce beneficial changes to cells that improve the health of the organism.

It is well observed that mild environmental stress often causes adaptive responses that lead to beneficial effects on the organism. While higher doses of an environmental stimulus may lead to toxic effects, small doses can promote health. The biphasic of environmental stress is termed "hormesis" and describes the beneficial effects of many stressors, including exercise. Exercise induces the production of ROS and RNS which can be toxic when produced in high quantities. Indeed, the immune system generates free radicals to kill pathogens. However, exercise is beneficial because it induces the generation of low levels of ROS/RNS causing adaptive changes in the cell that make it better prepared to deal with future stress (Radak, Z., Chung, H. Y. & Goto, S. Exercise and hormesis: oxidative stress-related adaptation for successful aging. *Biogerontology* 6, 71-75 (2005)).

There is a growing body of evidence showing that the activation of hormesis can be therapeutic in a wide range of diseases or adverse conditions, including diabetes mellitus, obesity, cancer, neurodegenerative disease, inflammation and aging (e.g. De Haes, W., et al. Metformin promotes lifespan through mitohormesis via the peroxiredoxin PRDX-2. Proceedings of the National Academy of Sciences 111, E2501 (2014); Cox, C. S., et al. Mitohormesis in Mice via Sustained Basal Activation of Mitochondrial and Antioxidant Signaling. *Cell metabolism* 28, 776-786.e775 (2018): Dugan, L. L., et al. AMPK dysregulation promotes diabetes-related reduction of superoxide and mitochondrial function. *The Journal of Clinical Investigation* 123, 4888-4899 (2013): Lark, D. S., et al. Enhanced Mitochondrial Superoxide Scavenging Does Not Improve Muscle Insulin Action in the High Fat-Fed Mouse. *PLOS ONE* 10, e0126732 (2015); Luna-López, A., González-Puertos, V. Y., López-Diazguerrero, N. E. & Königsberg, M. New considerations on hormetic response against oxidative stress. *Journal of cell communication and signaling* 8, 323-331 (2014); and Pearce, O. M., Läubli, H., Bui, J. & Varki, A. Hormesis in cancer immunology: Does the quantity of an immune reactant matter?Oncoimmunology 3, e29312-e29312 (2014)).

Our data show that magnetic non-parallel electric fields (MNPEFs) (see U.S. patent application Ser. No. 16/280,551, filed on Feb. 20, 2019, and titled THERAPEUTIC SYSTEMS USING MAGNETIC AND ELECTRIC FIELDS, which is incorporated herein by reference in its entirety) induce ROS formation, particularly superoxide, a highly reactive oxygen species. MNPEF driven induction of ROS leads to hormetic changes that improves the health of the animal. These hormetic changes include enhanced activity of the ROS scavenging enzyme glutathione (GSH), reduced activity and expression of mitochondrial complex I one of the major ROS producers in the cell, activation of the metabolism regulating enzyme, AMPK, and increased expression of the cytoprotective stimulating proteins, nuclear factor erythroid-derived 2-like 2 (Nrf2) and Keap-1. Treating animals with a superoxide specific scavenger throughout MNPEF therapy attenuated the beneficial effects of MNPEFs. These findings show that MNPEFs requires the generation of ROS and the induction of hormesis to elicit beneficial effects on metabolism. It is currently believed that magnetic non-parallel magnetic fields (MNPMF) will provide similar therapeutic benefits via the induction of hormesis and lowering of oxidative stress.

Free radicals are a target to treat a wide range of chronic disease, including diabetes, cancer, anti-aging, neurological and immune related disorders. Free radicals, including reactive oxygen species (ROS) and reactive nitrogen species (RNS) have been implicated in the pathogenesis of a wide range of chronic diseases. The majority of free radicals are produced in the mitochondria as a result of cellular respiration. Free radicals are also generated in other cellular compartments by various enzymes. Free radicals were once thought to be destructive to the cell, however, there is a growing body of evidence demonstrating that free radicals act as signaling molecules, transmitting crucial information that contributes to the health state of the cell. The following are references showing how free radicals are therapeutic targets for a wide range of disease.

Diabetes and Obesity

Free radicals, including ROS are linked to insulin resistance and obesity via oxidative stress and the redox state. ROS improves insulin sensitivity, depending on the cellular compartment where it is generated. Blocking the generation of ROS from cytoplasmic enzymes reduces insulin signaling and insulin sensitivity. ROS is also necessary for normal glucose stimulated insulin secretion. Metformin, an anti-diabetic medication alters ROS and the redox state to treat type 2 diabetes. Diabetic and obese patients have more oxidative stress compared to healthy controls. Human and animal studies have demonstrated that insulin sensitivity may be improved by decreasing oxidative stress or by inducing a reduced systemic redox state. Sutton, E. F., et al.

Early Time-Restricted Feeding Improves Insulin Sensitivity, Blood Pressure, and Oxidative Stress Even without Weight Loss in Men with Prediabetes. *Cell metabolism* 27, 1212-1221.e1213 (2018); De Mattia. G., et al. Influence of reduced glutathione infusion on glucose metabolism in patients with non-insulin-dependent diabetes mellitus. *Metabolism: clinical and experimental* 47, 993-997 (1998); Paolisso, G., et al. Plasma GSH/GSSG affects glucose homeostasis in healthy subjects and non-insulin-dependent diabetics. *American Journal of Physiology-Endocrinology and Metabolism* 263, E435-E440 (1992); Sekhar, R. V., et al. Gutathione Synthesis Is Diminished in Patients With Uncontrolled Diabetes and Restored by Dietary Supplementation With Cysteine and Glycine. *Diabetes Care* 34, 162 (2011). In addition, human studies have shown that obese patients have oxidative stress which is reduced following weight loss. Tumova, E., et al. The impact of rapid weight loss on oxidative stress markers and the expression of the metabolic syndrome in obese individuals. *Journal of obesity* 2013, 729515 (2013).

Cancer

An effective strategy for targeting cancer cells has been to target ROS and oxidative stress. Chemotherapy increases ROS leading to oxidative damage and the death of cancer cells. Platinum-based (e.g. cisplatin) significantly increase ROS to target tumors. Taxanes (e.g. paclitaxel) cause mitochondria to produce more ROS, leading to cell death. Radiation primarily damages DNA but also increases ROS which leads to further DNA damage, and cancer cell death. Metformin, which modulates redox and oxidative stress, has been shown to be effective in combination with radiation or chemotherapy in killing cancer. Trachootham, D., Alexandre, J. & Huang, P. Targeting cancer cells by ROS-mediated mechanisms: a radical therapeutic approach? *Nature Reviews Drug Discovery* 8, 579 (2009).

Anti-Aging

Aging in humans and animals is associated with an imbalance of ROS/RNS and oxidative stress. Increasing ROS moderately via exercise improves health in aging population due to the induction of adaptive changes that improve resilience to oxidative stress. Metformin, a redox modulator that reduces oxidative stress has anti-aging effects, extending lifespan and health span in mice. Metformin also show clinical benefits in aging human population, improved cardiovascular outcomes, reduction in mild cognitive impairment and dementia, and reduction in inflammation. Esteghamati, A., et al. Effects of metformin on markers of oxidative stress and antioxidant reserve in patients with newly diagnosed type 2 diabetes: a randomized clinical trial. *Clinical nutrition* (Edinburgh, Scotland) 32, 179-185 (2013); Fang, J., et al. Metformin alleviates human cellular aging by upregulating the endoplasmic reticulum glutathione peroxidase 7. *Aging Cell* 17, e12765 (2018).

Neurological

Like cancer and diabetes, many neurological diseases are linked to dysfunctional metabolism which causes dysregulation of ROS/RNS. Parkinson's disease (PD) progression is linked to mitochondrial dysfunction, ROS and oxidative stress. PD is caused by degeneration of dopaminergic neurons which leads to motor problems including uncontrolled shaking and muscle rigidity. Dopaminergic neurons use iron—leads to production of a lot of ROS that damages the neuron if not removed by antioxidants. Targeting ROS generated by iron is a new approach to treat PD. In addition, new therapies for PD targeting ROS may include using antioxidants (Vitamin E & C, CoQ10) to reduce ROS.

Alzheimer's disease (AD) and Amyotrophic lateral sclerosis (ALS) progression are linked to increased ROS/RNS and oxidative stress. Preclinical and clinical studies using drugs to reduce ROS show efficacy in managing AD and ALS. Drugs used for diabetes that target mitochondrial dysfunction are being repurposed to treat AD such as thiazolidinediones. ALS can be caused by a mutation in an antioxidant enzyme (SOD1) that reduces ROS. Tönnies, E. & Trushina, E. Oxidative Stress. Synaptic Dysfunction, and Alzheimer's Disease. *Journal of Alzheimer's disease: JAD* 57, 1105-1121 (2017); Carri, M. T., Valle, C., Bozzo, F. & Cozzolino, M. Oxidative stress and mitochondrial damage: importance in non-SOD1 ALS. *Frontiers in Cellular Neuroscience* 9, 41 (2015).

Immune and Inflammation

Inflammation/infection/immune response rely on pathways that are influenced by ROS/RNS and in turn, these pathways regulate ROS/RNS production. ROS/RNS stimulate the immune system to intensify the inflammatory response to kill microbes. The immune system uses inflammation and ROS/RNS to kill of bacteria and viruses that cause infection. Targeting ROS/RNS may be an effective method of enhancing the innate and/or adaptive immune system when fighting off an acute or chronic infection by bacteria or viruses. Alternatively, chronic inflammation causes diseases such as arthritis, lupus, dermatitis, and inflammatory bowel syndrome. Chronic inflammation can increase cancer incidence. Chen, Y., Zhou, Z. & Min, W. Mitochondria, Oxidative Stress and Innate Immunity. *Frontiers in Physiology* 9, 1487 (2018).

EMFs are a non-invasive method to modify the production and behavior cellular ROS and oxidative stress which we have shown can be used to treat disease (T1D, T2D, NSCLC).

Embodiments for Delivering Therapy Using Non-Parallel Magnetic Field(s)

Various embodiments of the present subject matter deliver a therapy by delivering energy to tissue. A magnetic field system may be configured to provide a magnetic field in a first direction to the tissue. The magnetic field system includes at least one magnetic field source to produce the magnetic field. The magnetic field produced by the at least one magnetic field source may include a magnetic field produced by at least one of a permanent magnet, a magnetic field produced by a temporary magnet or a magnetic field produced by electric current flow through a conductor. A second magnetic field system configured to provide a magnetic field in a second direction to the tissue, wherein the magnetic field system includes at least a second magnetic field source to provide a second magnetic field in a direction is non-parallel to the direction of the first magnetic field. Alternatively, the first magnetic field system may also be configured to provide the magnetic field in the second direction. The phrase "non-parallel" is defined as neither in the same direction nor in the opposite direction. Thus, directions that are non-parallel form an angle greater than 0 degrees and less than 180 degrees. For example, angles such as less than 170, 160, 150, 140, 130, 120, 110, 100, 90, 80, 70, 60, 50, 40, 30, 20 and 10 degrees can be used. The term "orthogonal" indicates that the directions form an angle that is 90 degrees, and substantially orthogonal indicates that the directions for an angle that is close to 90 degrees (e.g. 80 to 100 degrees, or 85 to 95 degrees). In some embodiments the angle between the first and second magnetic fields (e.g. DC magnetic field) can be described as orthogonal (90 degrees) or substantially orthogonal (such as between 80 and 100 degrees or between 85 and 95 degrees).

The term MNPMF refers to "Magnetic Non-Parallel Magnetic Field" and is defined as a magnetic field generated by a magnetic field system with at least one magnetic field source and a second magnetic field generated by the first or a second magnetic field system with at least one magnetic field source. Both the first and subsequent magnetic fields are delivered to targeted tissue (e.g. a volume of tissue). The vector direction of the magnetic field is non-parallel to the vector direction of the second magnetic field within the targeted tissue.

The term patient includes non-human animals and humans. Using the teachings provided herein the devices and methods described can readily be applied to a variety of patients, including for example, humans and companion animals such as dogs, cats, rabbits, hamsters, guinea pigs, pigs, horses and the like.

For purposes of this disclosure, the terms "treatment" and "management" (and similar references) may be used interchangeably. One of ordinary skill in the art will appreciate that treatment regimens include doses given over a period of days, weeks, months or throughout a patient's life time. A dose can be described as the amount of time (duration) that a patient is exposed to MNPMF that has a specified intensity (strength of the non-parallel magnetic fields) during a specified time period. For example, a patient can be exposed to a dose that is 10 hours in duration using a MNPMF of 3 mT in the first direction and 3 mT in the second direction every 24 hours. That dose can be given every day for 1 week, 2 weeks, three weeks or longer. The regime may shift to a shorter or longer dose, a less-frequent or more-frequency dose and/or a dose that is less intense or more intense. One of ordinary skill in the art will appreciate that the treatment regime can be designed by iteratively testing one or more of the physiological parameters described herein to assess the patient's response and then altering the regime as needed.

A magnetic field produced by an alternating current is a changing magnetic field as its direction and magnitude changes with time, whereas a magnetic field produced by a direct current is constant both in magnitude and direction. The terms $MNPMF^{DC/DC}$ refers to a static or non-varying magnetic field such as a magnetic field generated by a direct current in a wire, and a second static or non-varying magnetic field; and $MNPMF^{AC/DC}$ refers to a magnetic field that varies such as a magnetic field generated by an alternating current in a wire, and a second static or non-varying magnetic field. The first superscript refers to the type of magnetic field used in the first direction (DC, AC or a combination of the two) and the second term refers to the type of non-parallel magnetic field (DC, AC or a combination of the two). For example, a male patient may be exposed to $MNPMF^{AC/DC}$ and a female patient may be exposed to $MNPMF^{DC/DC}$ (when treating males and/or females) for from about 2-12 hours in a 24 hour period, or from about 3-10 hours, or from about 4-10 hours, or from about 6-8 hours in a 24 hour period. One of ordinary skill in the art will appreciate that the strength of the magnetic fields can also vary depending upon duration of the treatment and the overall physiological status of the patient. Initial dose ranging treatments can be used to establish the desired duration and intensity of the dose needed to achieve a desired outcome for an individual patient. Throughout this disclosure, "MNPMF" may refer generally to any MNPMF (e.g. $MNPMF^{DC/DC}$, $MNPMF^{DC/AC}$, $MNPMF^{AC/DC}$ or $MNPMF^{AC/AC}$.

FIG. 1 illustrates, by way of example and not limitation, a system 100 configured to deliver energy (e.g. MNPMF) to tissue as part of a therapy. The illustrated system includes a magnetic field system(s) 102 and 104. The magnetic field system 102 may be configured to provide a magnetic field B to targeted tissue, where a vector direction of the magnetic field in the targeted tissue is in at least a first direction. The letter B is conventionally used to denote a magnetic field or flux density, as illustrated in FIGS. 2B-2G for example. The term "magnetic" is also abbreviated herein with the letter M as used in the MNPMF term. It is noted that the magnetic field may, but need not be, uniform in direction throughout the tissue. That is, the magnetic field may have a complex shape within the tissue, such that the vector direction of the magnetic field within the tissue may vary depending on the position within the tissue. The magnetic field system 102 includes at least one magnetic field source 106 to produce the magnetic field. The magnetic field source(s) 106 may include permanent magnet(s). The magnetic field source(s) 106 may include temporary magnet(s). If a temporary magnet is used, the system will include means to magnetize the temporary magnet via another magnetic source. The magnetic field source(s) 106 may include conductor(s) through which electric current flows to create the magnetic field. The conductor may be a simple wire, a wire loop, or a coil of wire (such as a solenoid). The coil of wire may include a core to enhance the magnetic field generated by the electric current. For example, the magnetic field source(s) may include only one permanent or temporary magnet to produce the magnetic field, and the magnetic field source(s) may include at least two magnets (permanent or temporary), which may be located on opposing sides of the targeted tissue to produce the magnetic field in the first direction to the tissue. More complex arrangements are also contemplated. The magnetic field source(s) may include a conductor which is configured to generate the magnetic field in the first direction to the tissue when current flows through the conductor. The conductor may be a variety of shapes (e.g. line, loop, coil). The conductor may form part of a solenoid. A magnetic core within the coil may be used to strengthen the field. The current in the conductor which forms the magnetic field may be a direct current (DC) or alternating current (AC). Magnetic material with a high magnetic permeability may be used to confine and guide magnetic fields.

The magnetic field system 104 may include at least one magnetic field source 108 to provide the magnetic field in the second direction non-parallel to the first direction. In some embodiments, one magnetic field system may provide the magnetic field(s) in the first and second direction.

The magnetic field system(s) may be relatively simple systems that are always providing the magnetic fields. For example, a system may be designed using permanent magnets. The magnetic field system(s) may be more complex. By way of example, some system embodiments may include sensor(s) that may detect the presence of the patient in an environment (e.g. bed, chair, workstation), and turn on the system in response to detecting the patient's presence near the system. Some embodiments may turn on the system based on a clock/timer (e.g. 10:00 PM), and some embodiments may turn on the system in response to a detecting the patient's presence within a time window (e.g. 10:00 PM to 6:00 AM indicating the patient is in bed, or 9:00 AM to 5:00 PM indicating the patient is at a workstation). Sensor(s) may include a variety of position or motion sensor(s), such as a load sensor to register pressure changes that may be used to detect a patient lying in bed. Sensor(s) may also detect the physiological condition of the patient, which may be used to determine that the patient is in position for the therapy. Other examples may include a temperature sensor, an accelerometer to detect motion or posture, an impedance sensor, a sound sensor, a heart rate sensor, a respiration sensor and activity sensor.

Some system embodiments may include a controller 110 operably connected to at least one of the magnetic field systems 102 or 104. The controller 110 may include a scheduler 112 configured to control timing for generating at least one of the magnetic fields. The controller 110 may include one or more therapy programs 114 used to generate the MNPMF therapy. Each program may include a set of parameters used to generate the magnetic field(s). The set of parameter(s) may include one or more of an amplitude, frequency, pulse shape or source selection. Each of these parameter(s) may affect the resultant fields generated by the magnetic field system(s). Source selection for the magnetic field system may involve changing a location of a magnet or magnet(s), or energizing different conductor(s) from a plurality of conductors to change the field shape and vector direction of the field. Some embodiments may include mechanism(s) to physically move, rotate or re-orientate the magnetic source of the magnetic field system; and the therapy program(s) may implement processes to control those mechanism(s). Various programs may implement protocol(s) to adjust the absolute directions of magnetic field vector direction and/or adjust the relative angle between the magnetic field vector directions.

Some system embodiments may include a user interface 116. The user interface 116 may be configured for use by the user to create and/or modify one or more schedules 118 implemented by the controller 110. The user interface may be configured for use by the user to enter, select or adjust various magnetic field parameters 120 or 122 (indicating that the parameters may be independently adjusted for each of the magnetic field systems) such as parameter of the current used to create the magnetic field. These parameters may include amplitude, frequency, pulse shape. Other parameters may include duty cycle, duration, etc. The selectable parameters may include direction (e.g. source selection where selected sources control direction). The user interface may be configured for use by a user to control the start and/or end of the MNPMF therapy or portions thereof (e.g. start and/or stop the magnetic field(s) 124. The user interface may be configured for use by a user to control motion, rotation or orientation of the magnetic source(s) so as to enable user control of the absolute directions of magnetic field vector directions and/or the relative angle of the magnetic field vector directions. The start/stop control may be provided using, by way of example and not limitation, a mechanical button or switch or a selectable graphical user element on a display of the controller 110.

Figure 2:
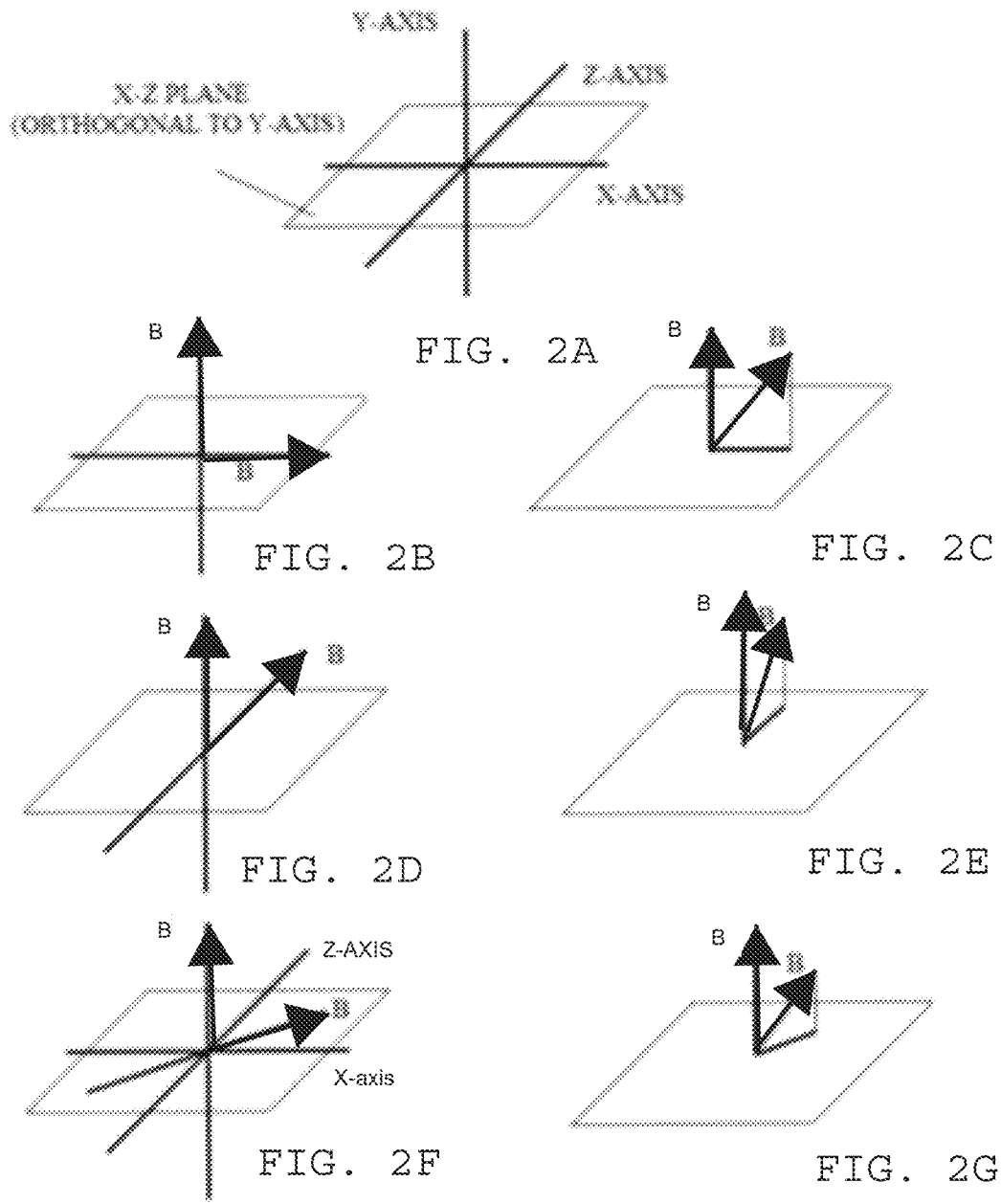
FIGS. 2A-2G illustrates, by way of example and not limitation, some non-parallel vector directions for the magnetic fields B.

FIGS. 2A-2G illustrates, by way of example and not limitation, some non-parallel vector directions for the magnetic fields B. FIG. 2A illustrates a 3-dimensional cartesian coordinate system with an X-axis, Y-axis, and Z-axis. In the illustrated figures, the vector direction of the magnetic field B is used as the reference and is placed along the Y axis. Of course, vector direction of the magnetic field B may be used as the reference, and the vector direction used as the reference may be placed in any orientation (e.g. on any of the axes). The X-axis and Z-axis define an X-Z plane that is orthogonal to the Y-axis direction.

FIG. 2B illustrates an example in which one magnetic field vector direction is along the Y-axis and another magnetic field vector direction is along the X-axis. This is an example of a MOMF as the vector direction of the magnetic field is orthogonal to the vector direction of the other magnetic field. FIG. 2C illustrates an example of a MNPMF, where the one magnetic field vector direction is along the Y-axis and another magnetic field vector direction is in the X-Y plane. The vector projection of the magnetic field on the X-Z plane is also illustrated. Since the vector projection is orthogonal to the Y-axis, this may be considered to be the contribution of the magnetic field to an MOMF. This also may be considered to be an indicator for a non-parallel and non-orthogonal field for a MNPMF therapy. Since there is a vector projection on the X-Z plane, the vector directions may be considered non-parallel.

FIG. 2D illustrates an example in which the magnetic field vector direction is along the Y-axis and the other magnetic field vector direction is along the Z-axis. This is another example of a MOMF as the vector directions are orthogonal. FIG. 2E illustrates an example of a MNPMF, where the magnetic field vector direction is along the Y-axis and another magnetic field vector direction is in the Y-Z plane. The vector projection of the magnetic field on the X-Z plane is also illustrated. Since the vector projection is orthogonal to the Y-axis, this may be considered to be the contribution of the magnetic field to an MOMF, and an indicator for a non-parallel and non-orthogonal field for a MNPMF therapy. Since there is a magnetic field vector projection on the X-Z plane, the magnetic field vector directions may be considered non-parallel.

FIG. 2F illustrates an example in which the magnetic field vector direction is along the Y-axis and another magnetic field vector direction is in the X-Z plane. This is another example of a MOMF as the vector direction of the magnetic field B is orthogonal to the vector direction of the second magnetic field B. FIG. 2F illustrates an example of a MNPMF, where the magnetic field vector direction is along the Y-axis and the other magnetic field vector direction is not in either the X-Y or Y-Z plane. The vector projection of the magnetic field on the X-Z plane is also illustrated. Since the vector projection is orthogonal to the Y-axis, this may be considered to be the contribution of the magnetic field to an MOMF, and an indicator for a non-parallel and non-orthogonal field for a MNPMF therapy. Since there is a vector projection on the X-Z plane, the magnetic field vector directions may be considered non-parallel.

All of the illustrated examples provide an acute angle between the vector directions that is more than 0 degrees and less than or equal to 90 degrees. The magnetic fields may be in an opposite direction such that the angle between the vector directions is less than 180 degrees but greater than or equal to 90 degrees.

According to various embodiments, the magnitude of the angle θ between the magnetic field vector directions is within a range where the range may be defined as: 0 degrees<θ<180 degrees: 1 degree≤θ≤179 degrees; 5 degrees≤θ≤175 degrees: 10 degrees≤θ≤170 degrees; 15 degrees≤θ≤165 degrees: 30 degrees≤θ≤150 degrees; 45 degrees≤<θ≤135 degrees: 60 degrees≤θ≤120 degrees: 80 degrees≤θ≤100 degrees; and 85 degrees≤θ≤95 degrees. According to various embodiments, the magnitude of the angle θ between the magnetic field vector directions is within a range where the range may be defined as: 0 degrees<θ≤90 degrees; 30 degrees≤θ≤90 degrees; 1 degree≤θ≤90 degrees; 5 degrees≤θ≤90 degrees; 10 degrees≤θ≤90 degrees; 15 degrees≤θ≤90 degrees; 30 degrees≤θ≤90 degrees; 45 degrees≤θ≤90 degrees: 60 degrees≤θ≤90 degrees; 80 degrees≤θ≤90 degrees: and 85 degrees≤θ≤90 degrees. According to various embodiments, the magnitude of the angle θ between the magnetic field vector directions is within a range where the range may be defined as: 90 degrees≤θ<180 degrees: 90 degrees≤θ≤179 degrees; 90 degrees≤θ≤175 degrees; 90 degrees≤θ≤170 degrees; 90 degrees≤θ≤165 degrees; 90 degrees≤θ≤150 degrees; 90 degrees≤θ≤135 degrees: 90 degrees≤θ≤120 degrees; 90 degrees≤θ≤100 degrees: and 90 degrees≤θ≤95 degrees.

According to various embodiments, the strength of the magnetic field may be within a range where: the range is 0 to 0.1 mT, the range is 0.1 mT to 1 mT, the range is 1 mT to 10 mT or the range is 10 mT to 100 mT. In some embodiments, the strength of the magnetic field may be in the range from 0 to 100 mT, the range from 0.1 mT to 10 mT, the range from 0.1 mT to 1 mT or the range from 1 mT to 10 mT. According to various embodiments, the strength of the magnetic field may be at least 0.5 mT, or within a range from 0.5 mT to 5 mT.

It is believed that there may be patient-to-patient variations, as body type (e.g. obese v. slender) and environment (e.g. number of conductors near patient) may affect the fields.

According to various embodiments, magnetic fields may have a frequency within a range from 0 to 100 Hz, 100 Hz to 1000 Hz, 1 kHz to 10 kHz, 10 kHz to 1000 kHz, and 1 MHz to 1000 MHz. It is noted that a frequency of 0 is constant field, and may be referred to as a DC (Direct Current) field. According to various embodiments, magnetic fields may have a frequency within a range from 0 to 1000 MHz, within a range from 100 Hz to 1000 MHz, within a range from 1 kHz to 1000 MHz, within a range from 10 kHz to 1000 MHz, within a range from 100 kHz to 1000 MHz, within a range from 100 Hz to 1 MHz, within a range from 1 kHz to 1 MHz, within a range from 10 kHz to 1 MHz, within a range from 100 kHz to 1 MHz, within a range from 100 Hz to 100 kHz, within a range from 1 kHz to 100 kHz, within a range from 10 kHz to 100 kHz, within a range from 100 Hz to 10 kHz, or within a range from 1 kHz to 10 kHz.

Figure 3:
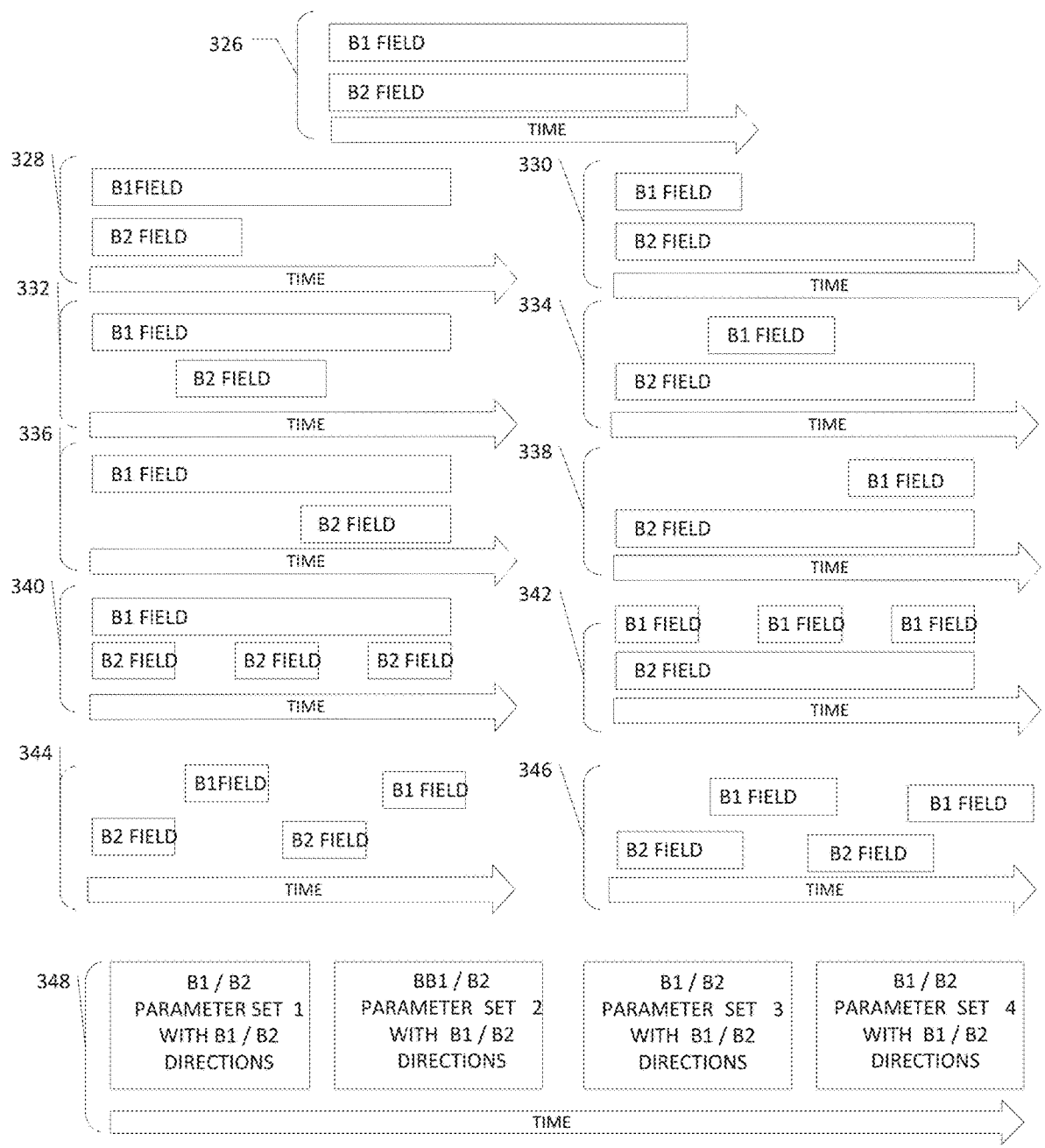
FIG. 3 illustrates, by way of example and not limitation, various timing diagrams for delivering the magnetic fields ("magnetic field component") for the MNPMF therapy.

FIG. 3 illustrates, by way of example and not limitation, various timing diagrams for delivering the magnetic fields ("magnetic field component") for the MNPMF therapy. These therapies may be initiated, for example, by manually or automatically switching on the magnetic field system. For example, some embodiments may be worn such as embodiments incorporated into articles of clothing (e.g. vests, caps, and the like) Some embodiments provide magnetic field components that are always on (e.g. permanent magnets). Some embodiments may provide magnetic field components that are always one or nearly always one upon set up, such as a system set up to deliver MNPMF therapy whenever the patient is in a certain environment (e.g. bed, chair, work station, under blanket, etc.). Some embodiments are programmed or otherwise automated to schedule delivery of at least one of the magnetic fields. Some embodiments operate only upon enabling conditions (e.g. at least one of time of day, detected patient location, detected patient posture, or detected patient activity or inactivity).

Timing diagram 326 illustrates concurrent delivery of the magnetic field components B1 and B2. The illustrated timing diagram 326 may, but does not necessarily, represent a dose (e.g. daily dose) of MNPMF. Both fields may be automatically or manually started and stopped at, or nearly at, the same times. As is also illustrated, the duration of the B1 and B2 components may be the same or approximately the same for a dose of MNPMF.

Timing diagram 328 illustrates that the B1 and B2 components are initiated at, or nearly at, the same time, but that the B2 component is terminated earlier than the B1 component. The illustrated timing diagram 328 may, but does not necessarily, represent a dose (e.g. daily dose) of MNPMF. As is also illustrated, the duration of the M1 component may be longer than the duration for the M2 component for a dose of MNPMF.

Timing diagram 330 illustrates that the B1 and B2 component are initiated at, or nearly at, the same time, but that the B1 component is terminated earlier than the B2 component. The illustrated timing diagram 330 may, but does not necessarily, represent a dose (e.g. daily dose) of MNPMF. As is also illustrated, the duration of the B2 component may be longer than the duration for the B1 component for a dose of MNPMF.

Timing diagram 332 illustrates that the B2 component is initiated after the B1 component and is terminated before the B1 component. The illustrated timing diagram 332 may, but does not necessarily, represent a dose (e.g. daily dose) of MNPMF. As is also illustrated, the duration of the B2 component may be shorter than the duration for the B1 component for a dose of MNPMF.

Timing diagram 334 illustrates that the B1 component is initiated after the B2 component and is terminated before the B2 component. The illustrated timing diagram 334 may, but does not necessarily, represent a dose (e.g. daily dose) of MNPMF. As is also illustrated, the duration of the B2 component may be longer than the duration for the M1 component for a dose of MNPMF.

Timing diagram 336 illustrates that the B2 component is initiated after the B1 component and is terminated when, or nearly when, the B1 component is terminated. The illustrated timing diagram 336 may, but does not necessarily, represent a dose (e.g. daily dose) of MNPMF. As is also illustrated, the duration of the B2 component may be shorter than the duration for the B component for a dose of MNPMF.

Timing diagram 338 illustrates that the B1 component is initiated after the B2 component and is terminated when, or nearly when, the B2 component is terminated. The illustrated timing diagram 338 may, but does not necessarily, represent a dose (e.g. daily dose) of MNPMF. As is also illustrated, the duration of the B2 component may be longer than the duration for the B1 component for a dose of MNPMF.

Timing diagram 340 illustrates that more than one instance of the B1 component may be provided when one instance of the B1 component is provided. One of the B2 components may, but need not, be initiated when the B1 component is initiated. Other embodiments initiate the B2 component before or after the B1 component is initiated. The illustrated timing diagram 340 may, but does not necessarily, represent a dose (e.g. daily dose) of MNPMF. The magnetic field B2 components may be periodically delivered, or may be scheduled or otherwise intermittently delivered for a dose of MNPMF.

Timing diagram 342 illustrates that more than one instance of the B1 component may be provided when one instance of the B2 component is provided. One of the B1 components may, but need not, be initiated when the B2 component is initiated. Other embodiments initiate the B1 component before or after the B2 component is initiated. The illustrated timing diagram 342 may, but does not necessarily, represent a dose (e.g. daily dose) of MNPMF. The magnetic field components may be periodically delivered, or may be scheduled or otherwise intermittently delivered for a dose of MNPMF.

Both timing diagram 344 and timing diagram 346 illustrate that multiple instances of the B2 component and B1 component may be delivered an interleaved with each other. Timing diagram 344 illustrates that the B2 component and B1 component do not overlap, whereas timing diagram 346 illustrates that the B2 component and B1 component do overlap. Each of the illustrated timing diagrams 334 and 336 may, but does not necessarily, represent a dose (e.g. daily dose) of MNPMF. Also, it is noted that interleaved instances of the B2 components and M1 components do not have to have a 1:1 ratio. That is, B2 components may be interleaved with B1 components where there are fewer B2 components than B1 components, and B12 components may be interleaved with B2 components where there are fewer B1 components.

Timing diagram 348 illustrates that multiple programs may be delivered over a time period. A programmed schedule may control when each program is initiated and terminated, within each program, there timing between the B1 and B2 component(s) may be controlled, such as illustrated in but not limited to timing diagrams 326, 328, 330, 332, 334, 336, 338, 340, 342, 344 and 346. Each program may be considered to be a distinct parameter set for at least one of the B1 component or B2 component. Each of the programs may keep the same magnetic field vector directions, but change other parameters such as amplitude, pulse shape, frequency, etc. In some embodiments, at least some of the programs change the magnetic field vector direction for at least one of the B1 component or the B2 component, with or without other parameter changes. The magnetic field vector direction changes may cause the relative angle between the magnetic field vector directions to change. In some embodiments, the magnetic field vector direction changes are designed to change the absolute angle with respect to the targeted tissue, but keep the same or nearly the same relative angle between the magnetic field vector direction for the B1 or B2 component. Vector directions may be changed by selecting different magnetic field source(s). By way of example and not limitation, differently-positioned and/or shaped conductor(s) may be energized to conduct current to change the magnetic field vector direction. Some embodiments may include mechanism(s) to physically move, rotate or re-orientate the magnetic source of the magnetic field system; and the therapy program(s) may implement processes to control those mechanism(s).

Figure 4:
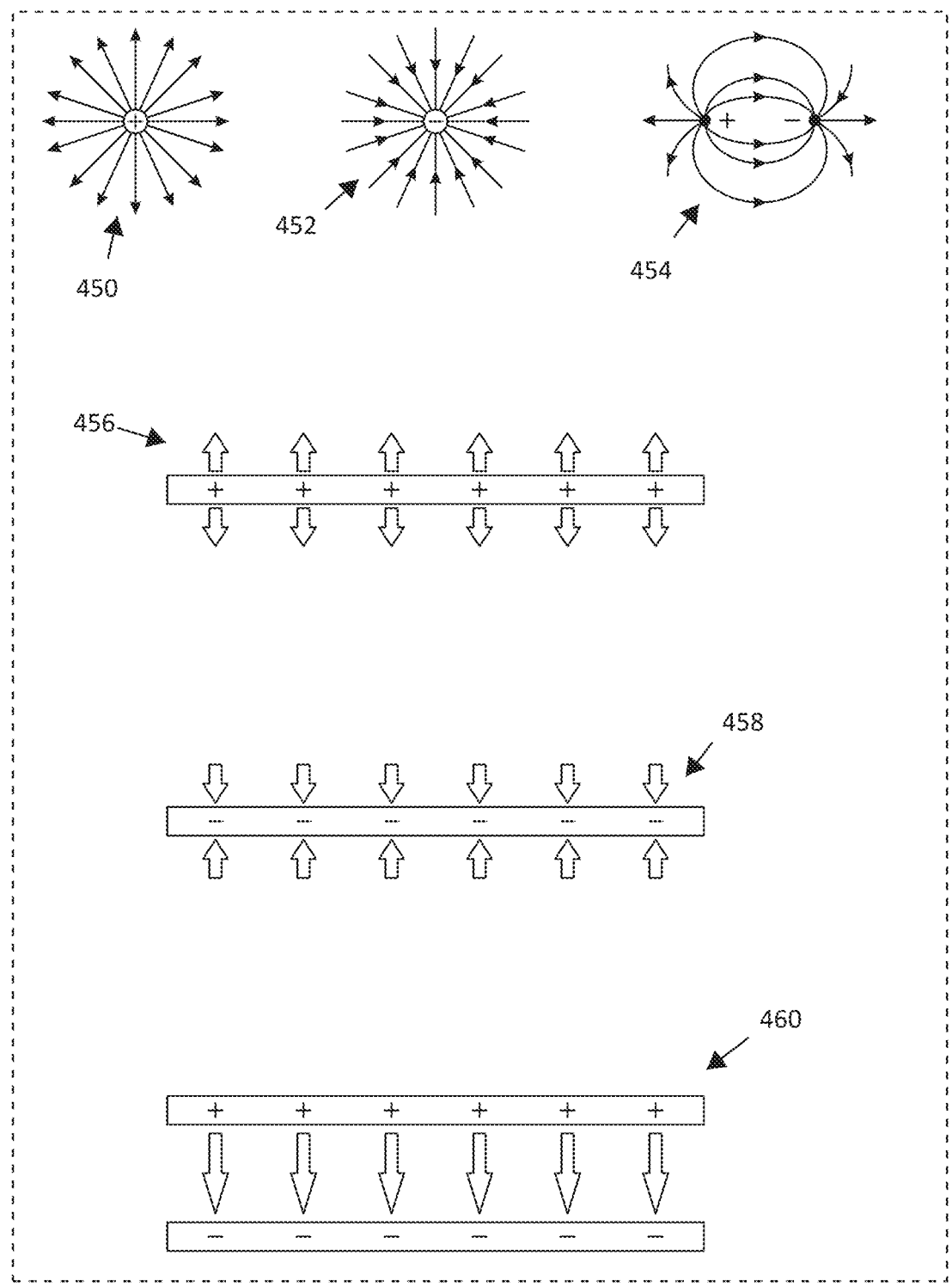
FIG. 4 illustrates, by way of example and not limitation, various examples of electric field shapes that may be generated by different electrode shapes and different charges applied to the electrode shapes, as some embodiments may also deliver an electric field in combination with the two or more non-parallel magnetic field vector direction associated with the MNPMF therapy.

The present subject matter delivers MNPMF therapy to achieve the benefits described herein. Some embodiments may also deliver an electric field in combination with the two or more non-parallel magnetic field vector direction associated with the MNPMF therapy. Electric field source(s) and magnetic field source(s) may be configured and positioned to provide the desired vector fields in the targeted tissue. FIG. 4 illustrates, by way of example and not limitation, various examples of electric field shapes that may be generated by different electrode shapes and different charges applied to the electrode shapes. A small, circular button electrode may produce a similar electric field as a point charge. An electric field for a positive point charge is illustrated at 450, and an electric filed for a negative point charge is illustrated at 452. Some embodiments may provide the electric field in a monopolar configuration in which only one electrode is positioned to provide the electric field to the targeted tissue. The reference/return electrode may be positioned away from the electrode such as on the housing of the stimulator device. An electric field for a dipole, consisting of a positive point charge and a negative point charge, is illustrated at 454. It is noted that the electric field lines between the dipole become more linear. Thus, the dipole may be positioned so that the targeted tissue is generally centered on the dipole. Some embodiments may use one or more plate-shaped electrodes. One positively-charged, plate-shaped electrode is illustrated at 456, and one negatively-charged, plate-shaped electrode is illustrated at 458. the electric field extends generally uniformly from the surface of the plate. Some embodiments may use two oppositely-charged, plate-shaped electrodes to provide a relatively uniform and focused electric field between the two plates, as generally illustrated at 460. The oppositely-charged, plate-shaped electrodes may be placed on opposing sides of the targeted tissue (or on opposing sides of the patient) so that the fields extend through the targeted tissue.

Figure 5:
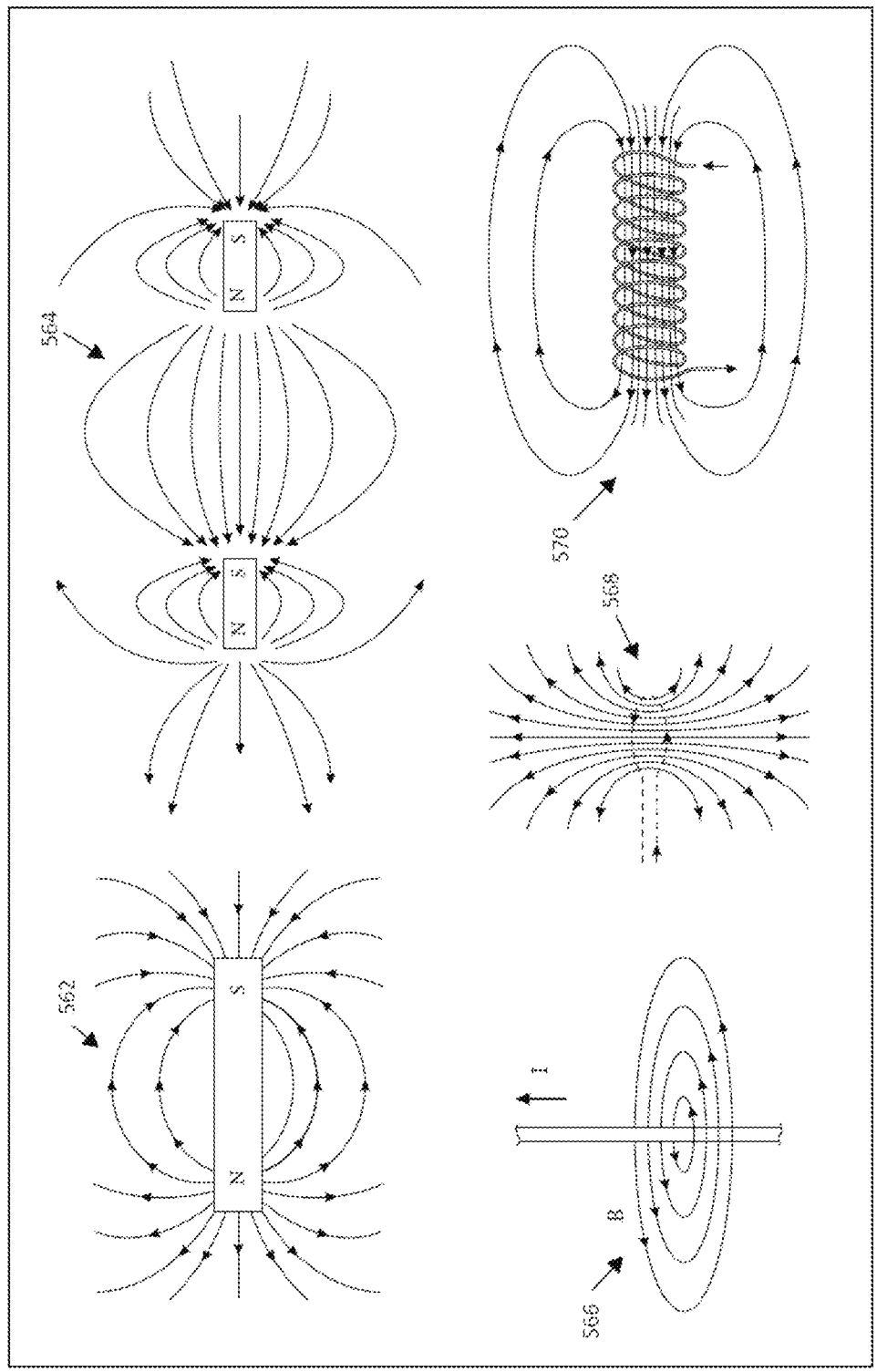
FIG. 5 illustrates, by way of example and not limitation, various examples of magnetic field shapes that may be generated by different magnetic field sources.

FIG. 5 illustrates, by way of example and not limitation, various examples of magnetic field shapes that may be generated by different magnetic field sources. The magnetic source(s) may be, but do not have to be, positioned so that approximately linear magnetic field vectors pass through the targeted tissue. The magnetic field lines for a simple bar-type magnet is illustrated at 562. The vector directions of the magnetic field approximate linear vectors between the two poles and adjacent to the magnet, or adjacent to the two poles on the end of the magnet. The magnetic field lines for two magnets is illustrated at 564. The vector directions of the magnetic field approximate linear vectors between the two magnets. The magnetic field B lines induced by current flow (I) through a conductor is generally illustrated at 566. The induced magnetic field is generally concentric about the wire. The conductor may be positioned and shaped to provide the desired magnetic field to the targeted tissue. For example, current flow through a conductor loop generates a magnetic field as generally illustrated at 568, and current flow through a coiled conductor generates a magnetic field as generally illustrated at 570. A solenoid, for example, uses current flow through a tightly wound coil of wire to provide a magnetic field. Additional materials inside and outside of the coil may be used to further shape the magnetic field.

Figure 6:
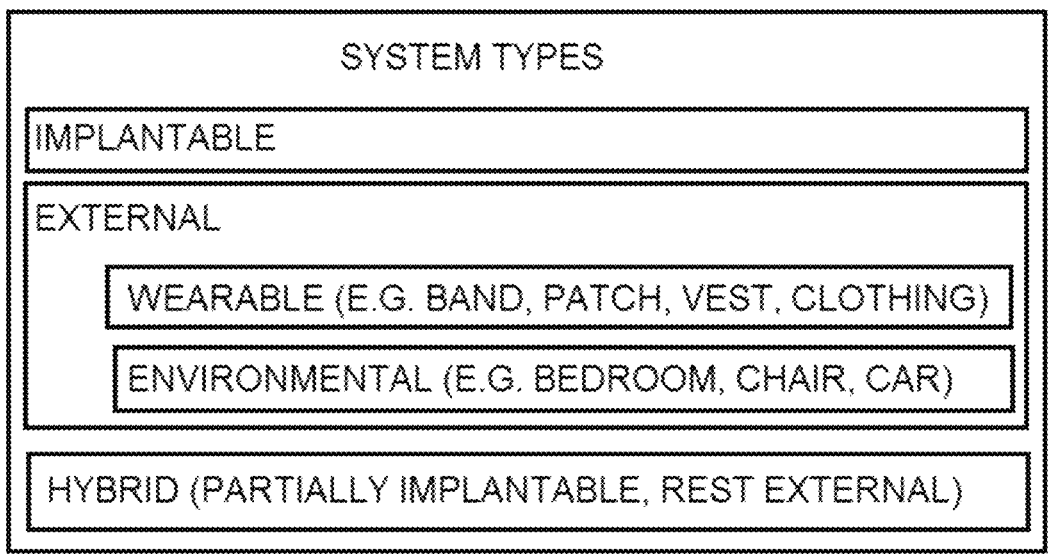
FIG. 6 illustrates different system types for the MNPMF system.

FIG. 6 illustrates different system types for the MNPMF system. The magnetic field system may be an implantable system including all implantable components, or may be an external system including all external components, or may be a hybrid system where only some of the components are implantable the remainder or external. Similarly, the magnetic field system may be an implantable system including all implantable components, or may be an external system including all external components, or may be a hybrid system where only some of the components are implantable the remainder or external. Implantable systems may be used to deliver the MNPMF therapy to an ambulatory patient. External systems may be wearable systems or environmental systems. A wearable system is configured to be carried by an ambulatory patient. The system may be incorporated into a band or strap that can be secured around a patient or at least a targeted body part of the patient, a patch that can be adhered to the skin or otherwise secured to the patient's body, a vest, a cap, or other article of clothing and a component attached to the clothing. Environmental systems are designed to be set up in an environment that the patient is in on a regular basis. Thus, a bedroom, chair, work station, or car are examples of environments that may be set up with a magnetic field system(s) to deliver the MNPMF therapy. The MNPMF therapy may be externally applied to the ambulatory patient. A hybrid system includes some implantable components. For example, the magnet(s) or current conductors used by the magnetic field system may be implanted to more precisely target the magnetic field to the targeted tissue. The controller 110 illustrated in FIG. 1 may be implantable, may be external or may be distributed so as to be partially implantable and partially external. An example of a distributed controller may include a separate controller for each magnetic field system, where each controller performs some of the functions to deliver the MNPMF therapy.

The system may be configured, according to various embodiments, to collect data regarding patient adherence. This data may reflect the duration that the MNPMF therapy is delivered, or another indicator of a delivered therapy dose over time periods. For an environmental system such as a bed, the system may use a sensor to register pressure changes indicating patient is in bed. Other sensor(s) may be used to detect location. The system may track on/off times and/or energy use when the patient is in the environment for the therapy. A wearable device may register current flow or temperature to indicate whether the device is worn properly. Wearable device and implantable devices may track on/off times and energy use. Data can be transmitted to device(s) used by physicians, patient or another party to track patient adherence. Data can be displayed on the device and/or transmitted via near field communication (NFC), Bluetooth, wireless internet or wireless transfer of another kind.

Some system embodiments may include sensor(s) worn by the patient to detect the magnetic fields, which may be used to indicate when therapy is being delivered to patient. The sensor data may be stored and/or transmitted to device(s) used by physicians, patient or another party to track patient adherence. The sensor(s) may simply track when the patient is in an environment when the strength of the field(s) are above a threshold. The sensor(s) may also determine and track dosing information. The sensor(s) may also determine and track the strength of the field(s) and/or the absolute and/or relative direction of the field(s). Some embodiments use this information to calibrate the MNPMF therapy for patient. Information from other patients (including dosing information and/or therapeutic effects of the MNPMF therapy) may also be used to calibrate the MNPMF therapy for individual patients. Sensor(s) used to track dosing may be externally worn or may be implanted proximate to the targeted tissue, regardless of whether the fields are internally or externally generated.

Figure 7:
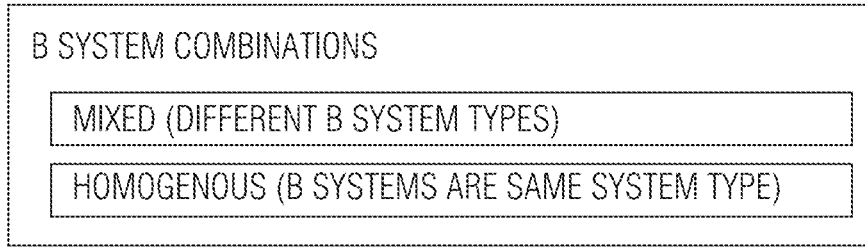
FIG. 7 illustrates combinations for types of magnetic field systems.

FIG. 7 illustrates for types of magnetic field system types. A mixed system combination indicates that one of the magnetic field systems is one of the implantable, external (wearable or environmental) or hybrid types, and the other one is another one of the implantable, external (wearable or environmental) or hybrid types. A homogenous system combination indicates that both magnetic field systems are the same system type (implantable, external (wearable or environmental) or hybrid types).

Figure 8:
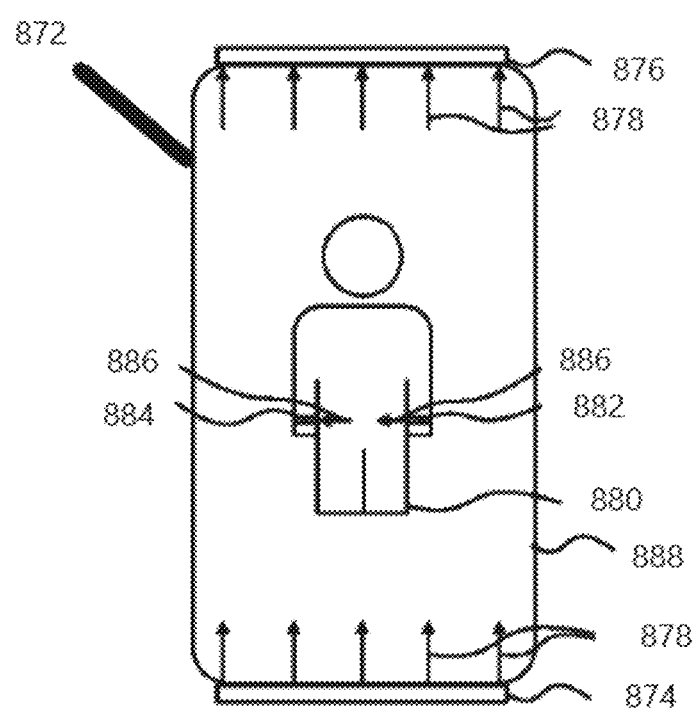
FIG. 8 illustrates, by way of example and not limitation, a schematic diagram illustrating a system for delivering MNPMF.

FIG. 8 illustrates, by way of example and not limitation, a schematic diagram illustrating a system 872 for delivering MNPMF. The system 872 may comprise a direct current (DC) magnetic field system 874, 876 that generates and applies a DC magnetic field 878 to a patient 880: and a DC magnetic field system 882, 884 that generates and applies a DC magnetic field 886 to the patient 880 in a field direction substantially orthogonal to a direction of the DC magnetic field 878. The system 872 may be implemented in an environment of a bed 888.

Figure 10B:
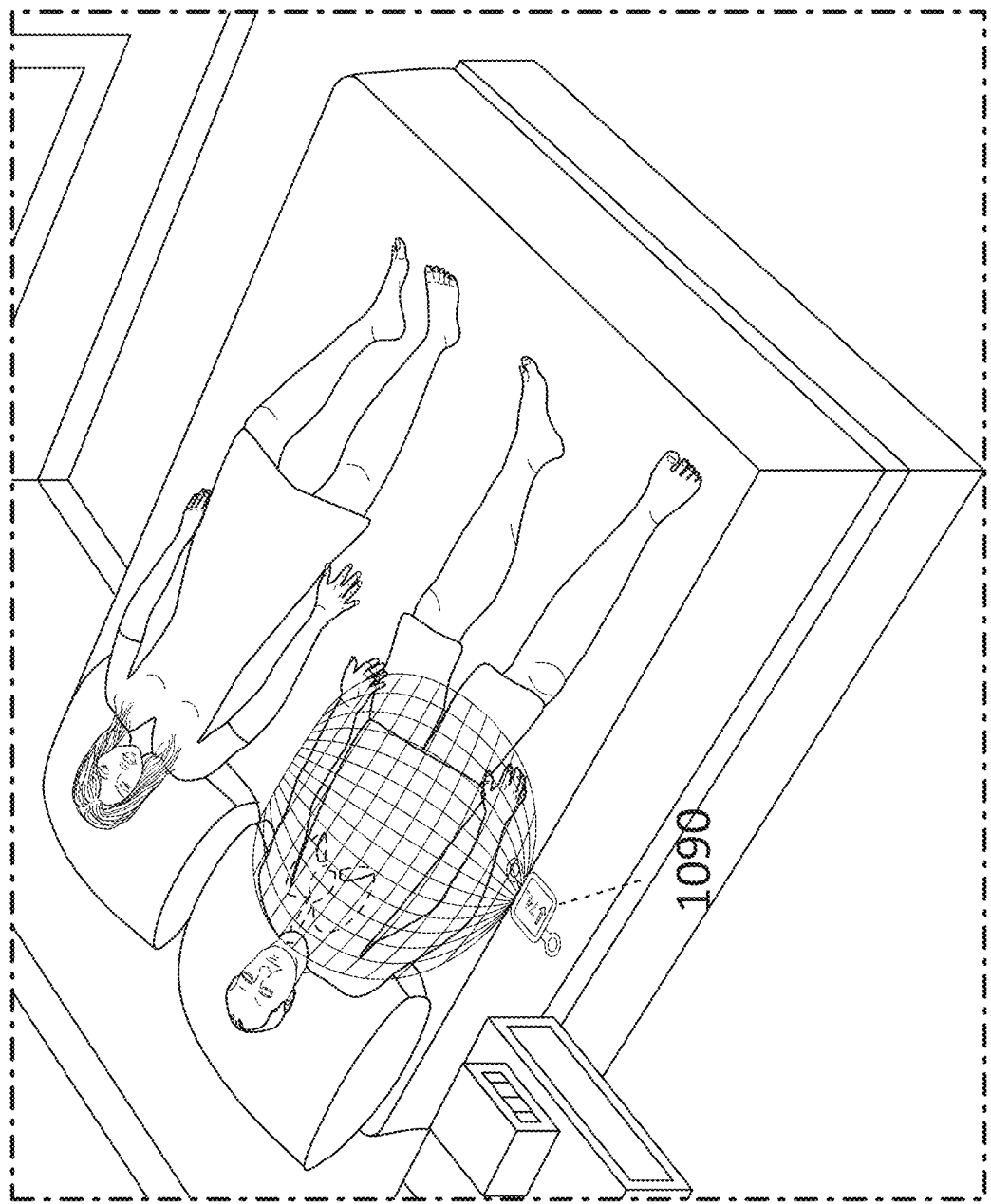

FIGS. 9A-9B illustrate, by way of example and not limitation, embodiments of a system in the form of a patch-like device. The system illustrated in FIG. 9B generally includes the same components as the system in FIG. 9A. The size and shape of the device may be engineered to provide the desired magnetic fields. The device 990 may include magnets and/or current induced magnets 992 that function as the magnetic field source. The device 990 may also include a magnetic field source 994, which may be implemented as permanent magnets within the device housing or may be implemented as a current-induced magnet within the device. For example, some embodiments using a conductor loop (or coiled conductor) around the perimeter of the device housing to generate a magnetic field generally orthogonal to the major surfaces of the device. The device may be incorporated to perform other functions. For example, the illustrated device provides a blood glucose readout 996, which may be obtained (e.g. via wireless communication) from a glucose sensor (finger prick meter or wearable continuous blood glucose sensor). Some embodiments incorporate a blood-glucose sensor into the device so that the blood glucose sensor may be percutaneously inserted to the patient. FIGS. 10A-10B illustrate the patch-like device of FIG. 9A implemented as a wearable device adhered or otherwise attached directly or indirectly to the patient and as an environmental device under the bed mattress, respectively. Other patient parameter(s) (e.g. biomarker(s)) may be sensed to indicate the state of the disease or patient condition. The patient parameter(s) may be directly indicative of a symptom of the disease or condition, or may be a surrogate of a parameter indicative of a symptom of the disease or condition.

Figures 11A, 11B, 11C:
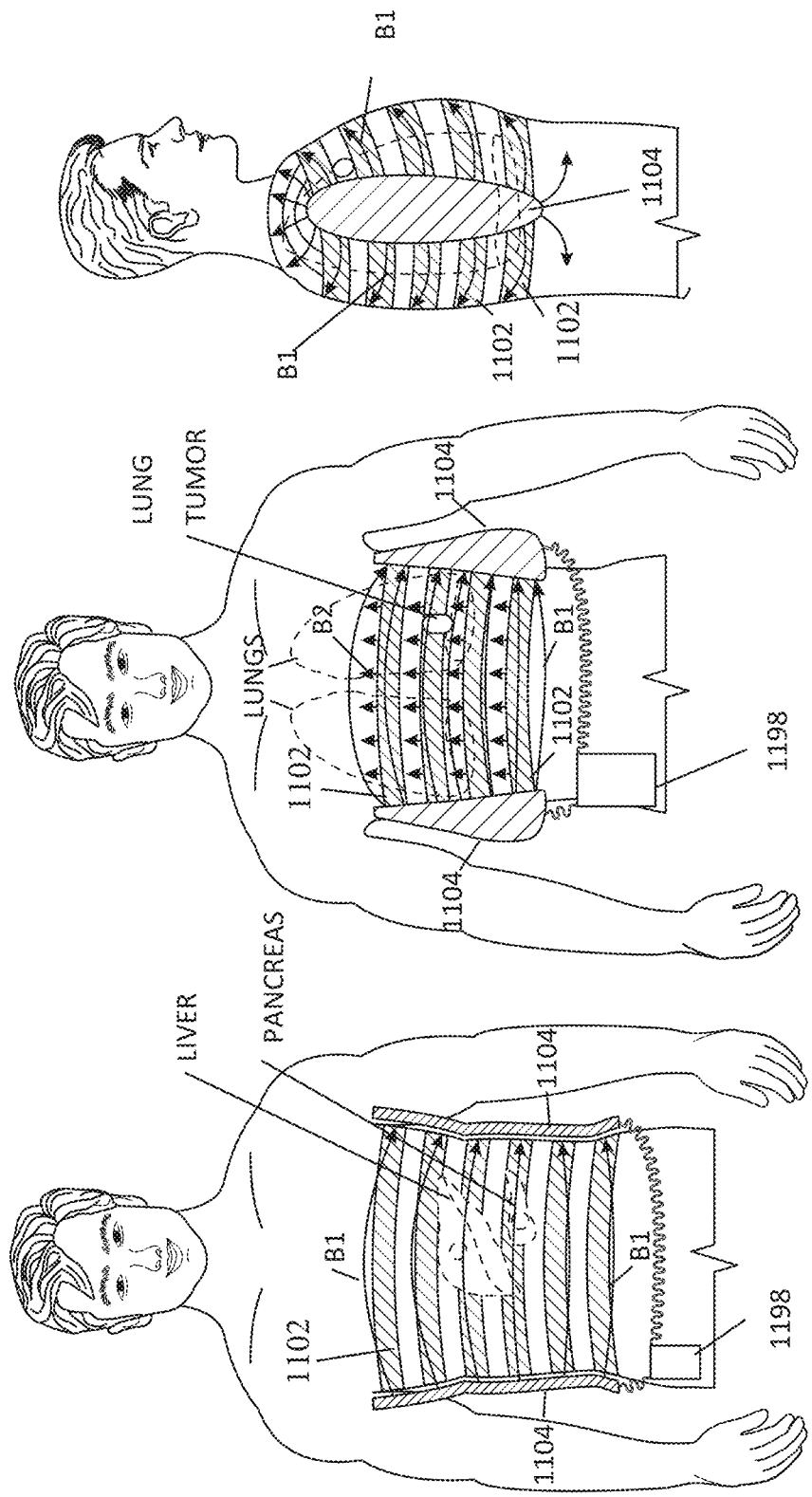
FIGS. 11A-11C illustrate an embodiment of a wearable MNPMF system in the form of vest.

FIGS. 11A-11C illustrate an embodiment of a wearable MNPMF system in the form of vest. FIG. 11A illustrates that the vest is configured to deliver the MNPMF therapy to the liver and/or pancreas such as may be useful as a therapy for diabetes. The depicted embodiment may also be configured to deliver MNPMF therapy to a tumor residing within tissues in the abdomen (e.g. liver, pancreas, stomach, gallbladder, sarcoma, intestines and/or prostate). FIG. 11B illustrates that the vest is configured to deliver the MNPMF therapy to a cancerous tumor in the lung. FIG. 11C illustrates a side view of the vest. The system may include a power source or sources 1198 to provide some the magnetic field system embodiments. The magnetic field system(s) may comprise permanent magnets or may comprise a conductor wrapped in a coil 1102 such that the coil surrounds the patient when worn. The magnetic field vector may be in the rostral-caudal direction (e.g. toward the head). Another one of the magnetic field systems may include two magnets 1104 on opposing sides of the patient (e.g. one plate-shaped electrode under each arm) electrically-connected to the power source 1198. The magnetic field vectors may be oriented to be approximately orthogonal. However, the system may be engineered to provide the fields in other non-parallel vector directions.

FIG. 12 illustrates an embodiment of a wearable MNPMF system as an article to be worn on the head. For example, the wearable device may be incorporated into a hat or a head band. Similar to the vest illustrated in FIGS. 11A-11c, the MNPMF system to deliver therapy to the head may include a power source or sources 1198 to provide electrical power for magnetic field system(s). The magnetic field system(s) may comprise permanent magnets or solenoids 1202, and magnets or solenoids 1204. The solenoids or magnets 1202 may be oriented to provide magnetic field vectors B2 in the lateral direction, and the magnetic field vectors B1 in the anterior-posterior direction. However, the system may be engineered to provide the fields in other non-parallel vector directions.

FIGS. 13A-13B illustrate an embodiment of an implantable MNPMF system, illustrated by way of example and not limitation, around a tumor in an arm. The implantable device 1306 may include a power source or sources 1308, solenoid(s) or magnet(s) 1310 to generate a magnetic field B2, and solenoid(s) or magnet(s) 1312 on opposing sides of the tumor to generate a magnetic field B1. The solenoids or magnets 1310 and 1312 may be oriented to provide orthogonal, or approximately orthogonal, magnetic field vector directions. However, the system may be engineered to provide the fields in other non-parallel vector directions.

FIGS. 14A-14B illustrate an embodiment of an environmental MNPMF system, illustrated by way of example and not limitation, around a patient's bed. The system may include a power source or sources 1414 to provide electrical power for the magnetic field system(s). The magnetic field system(s) may comprise permanent magnets or solenoids 1416 along the sides of the bed (e.g. attached to the bed or bedframe), and permanent magnets or solenoids 1418 above and/or beneath the patient. The solenoids or magnets 1418 beneath the patient may also be beneath a pad or mattress. The solenoids or magnets 1416 may be oriented to provide magnetic field vectors B2 in the lateral direction, and the solenoids or magnets 1418 may be oriented to provide the magnetic field vectors B1 in the vertical direction (e.g. dorsal-ventral if patient is lying on back). However, the system may be engineered to provide the fields in other non-parallel vector directions.

FIGS. 15A-15B illustrate an embodiment of an environmental MNPMF system, illustrated by way of example and not limitation, around a patient's bed. The system(s) may include a power source or sources 1514 to provide electrical power for the magnetic field system(s). The magnetic field system may comprise permanent magnets or solenoids 1516 along the sides of the bed (e.g. attached to the bed or bedframe), and oriented to provide magnetic field vectors B2 in the lateral direction, and may comprise permanent magnets or solenoids 1518 oriented to provide the magnetic field vectors B1 in the longitudinal direction (e.g. superior-inferior or rostral-caudal). However, the system may be engineered to provide the fields in other non-parallel vector directions.

Figure 16:
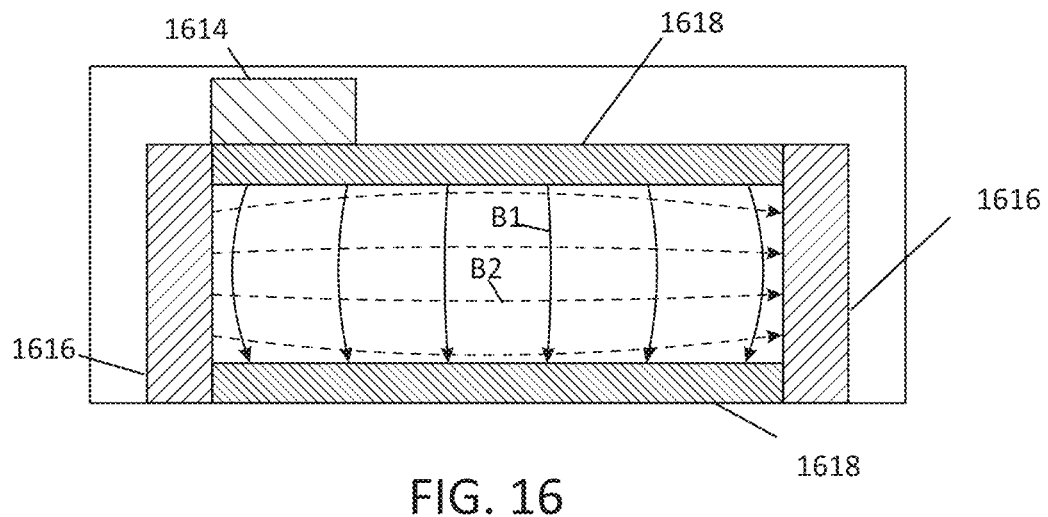
FIG. 16 illustrates an embodiment of an environmental MNPMF system, illustrated by way of example and not limitation, incorporated into furniture such as a couch.

FIG. 16 illustrates an embodiment of an environmental MNPMF system, illustrated by way of example and not limitation, incorporated into furniture such as a couch. FIG. 16 illustrates a top view of the couch. The system(s) may include a power source or sources 1614 to provide electrical power for the magnetic field system(s). The magnetic field system may comprise permanent magnets or solenoids 1616 along the sides of the couch, and permanent magnets or solenoids 1618 on the back of the couch. The solenoids or magnets 1616 may be oriented to provide magnetic field vectors B2 in the lateral direction, and the permanent magnets or solenoids 1618 may be oriented to provide the magnetic field vectors B1 in a direction from the back of the couch to the front. However, the system may be engineered to provide the fields in other non-parallel vector directions.

Figures 17A, 17B:
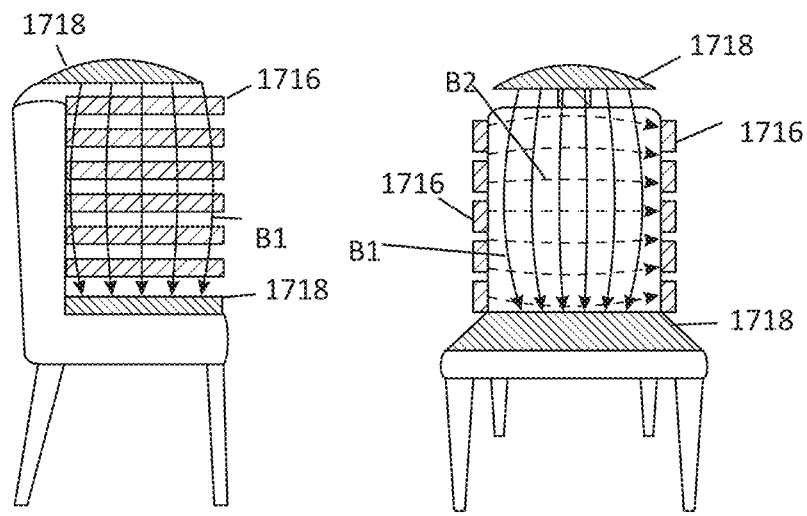
FIGS. 17A-B illustrate an embodiment of an environmental MNPMF system, illustrated by way of example and not limitation, incorporated into furniture such as a chair.

FIGS. 17A-17B illustrate an embodiment of an environmental MNPMF system, illustrated by way of example and not limitation, incorporated into furniture such as a chair. The system may include a power source or sources 1714 to provide electrical power for the magnetic field system(s). The magnetic field system(s) may comprise permanent magnets or solenoids 1716 along the sides of the backrest of the chair, and permanent magnets or solenoids 1718 on the seat of the chair. Some embodiments may further provide electrode(s) over the chair extending off of the backrest. The solenoids or magnets 1716 may be oriented to provide magnetic field vectors in the lateral direction, and the electrodes 1718 may be oriented to provide the second orthogonal magnetic field vectors in a direction from the top of the chair to the seat. However, the system may be engineered to provide the fields in other non-parallel vector directions.

A system may include a machine in the example form of a computer system, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by one or more processors (e.g., a computer) to individually or jointly execute instructions to perform any one or more of the methodologies discussed herein.

An example of a computer system may include components such as at least one processor (e.g., a central processing unit (CPU), a graphics processing unit (GPU) or both, processor cores, compute nodes, etc.), a main memory and a static memory, which communicate with each other via a link (e.g., bus). Components of a computer system may include a video display unit, an alphanumeric input device (e.g., a keyboard), and a user interface (UI) navigation device (e.g., a mouse). The video display unit, input device and UI navigation device may be incorporated into a touch screen display. Components of a computer system may include a storage device (e.g., a drive unit), a signal generation device (e.g., a speaker), a network interface device, and one or more sensors. It will be understood that other forms of machines or apparatuses (such as IPG, RC, CP devices, and the like) that are capable of implementing the methodologies discussed in this disclosure may not incorporate or utilize every one of these components (e.g. may not incorporate a GPU, video display unit, keyboard, etc.).

The storage device includes a machine-readable medium on which is stored one or more sets of data structures and instructions (e.g., software) embodying or utilized by any one or more of the methodologies or functions described herein. The instructions may also reside, completely or at least partially, within the main memory, static memory, and/or within the processor during execution thereof by the computer system, with the main memory, static memory, and the processor also constituting machine-readable media. The term "machine-readable medium" may include a single medium or multiple media (e.g., a centralized or distributed database, and/or associated caches and servers) that store the one or more instructions. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM) and flash memory devices; magnetic disks such as internal hard disks and removable disks; magneto-optical disks: and CD-ROM and DVD-ROM disks.

The instructions may further be transmitted or received over a communications network using a transmission medium via the network interface device utilizing any one of a number of well-known transfer protocols (e.g., HTTP or Bluetooth®). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

Biomarkers

The biological effects of MNPEFs and MNPMFs are mediated by interaction with redox and metabolic systems. Carter C. S., Huang. S. C., Searby C. C., Cassaidy B., Miller M. J., Grzesik W. J., Piorczynski T. B., Zhang Q., Bradberry K., Pak T. K., Walsh S. A., Dick D. W., Akurathi V., Acevedo M., Mapuskar K. A., Milne G. L., Hinton A. O., Guo D. F., Falls-Hubert K. C., Wagner B. A., Carter W. A., Wang K, Norris A. W., Rahmouni K., Buettner G. R., Hansen J. M., Spitz D. R, Abel E. D. and Sheffield V. C. Static magnetic and electric fields treat type 2 diabetes via redox dependent mechanisms. *Cell metabolism* Accepted (2020). Monitoring treatment efficacy is important to establish safe and effective dosing parameters. Fortunately, there are robust and chemically stable biomarkers within redox and metabolic systems that are useful as indicators of the biological and therapeutic efficacy of MNPEFs and MNPMFs. These include biomarkers of glucose metabolism, lipid peroxidation and oxidative stress which may be used individually or in combination to detect a positive therapeutic response of MNPEFs and/or MNPMFs: glucose, insulin, glucagon, HbA1c, c-peptide, pyruvate, lactate, FGF21, GDF15, adiponectin, cortisol, F2-isoprostanes (e.g. 5-series, 12-series, 8-series and 15-series), a product of free radical mediated oxidation of arachidonic acid (see Sampson, M. J., Gopaul, N., Davies, I. R., Hughes, D. A. & Carrier, M. J. Plasma F2 Isoprostanes. *Diabetes Care* 25, 537 (2002); Milne, G. L., Sanchez, S. C., Musiek, E. S. & Morrow, J. D. Quantification of F2-isoprostanes as a biomarker of oxidative stress. *Nature protocols* 2, 221-226 (2007); Il et al. Urinary F2-Isoprostanes as a Biomarker of Reduced Risk of Type 2 *Diabetes. Diabetes Care* 35, 173 (2012)), antioxidants such as the glutathione (GSH), glutathione disulfide (GSSG), cysteine (Cys), cystine (CysS), thioredoxin (Trx), peroxiredoxin (Prdx), glutathione-S-transferase (GST), glutathione peroxidase 3 (GPX3) which participate in neutralizing oxidants by supporting or directly donating reducing equivalents to reduce and neutralize oxidants (see Jones, D. P. Radical-free biology of oxidative stress. *Am J Physiol Cell Physiol* 295, C849-C868 (2008); Jones, D. P. & Sies, H. The Redox Code. *Antioxidants & redox signaling* 23, 734-746 (2015); Harris, I. S., et al. Glutathione and thioredoxin antioxidant pathways synergize to drive cancer initiation and progression. *Cancer cell* 27, 211-222 (2015): Hauffe, R., et al. GPx3 dysregulation impacts adipose tissue insulin receptor expression and sensitivity. *JCI Insight* 5(2020)), expression of genes that induce the antioxidant response: NRF2, which translocates to the nucleus upon activation by oxidative stimuli where they induce expression of genes that mediate an antioxidant response (see Kansanen, E., Kuosmanen, S. M., Leinonen, H. & Levonen, A.-L. The Keap1-Nrf2 pathway: Mechanisms of activation and dysregulation in cancer. *Redox Biol* 1, 45-49 (2013); Schmidlin, C. J. Dodson. M. B., Madhavan, L. & Zhang, D. D. Redox regulation by NRF2 in aging and disease. *Free Radical Biology and Medicine* 134, 702-707 (2019)), expression of genes that are activated by NRF2 to mediate the antioxidant response: NAD(P)H dehydrogenase [quinone] 1 (NQO1), heme oxygenase 1 (HMOX1), glutamate-cysteine ligase catalytic subunit (GCLC), glutamate-cysteine ligase regulatory subunit (GCLM) (see Kansanen et al.), the redox couples, NADP+, NADPH, NAD+, NADH, redox post-translational modifications such as glutathionylation, cysteinylation, nitrosylation, carbonylation etc. 6, long-chain fatty acids (LCFAs) (e.g. myristate, myristoleate, pentadeconoate, palmitate, palmitoleate, margarate, 10-heptadecenoate, stearate, oleate, vaccinate, nonadecanoate, 10-nonadecenoate, arachidate, eicosenoate, erucate etc.), poly unsaturated fatty acids (PUFAs) (e.g. heneicosapentaenoate, tetradecadienoate, hexadecadienoate, hexadecatrienoate, stearidonate, eicosapentaenoate, docasapentaenoate, docosahexaenoate, docosatrienoate, nisinate, linoleate, linolenate, dihomo-linolenate, arachidonate, adrenate, docosapentaenoate, docosadienoate, dihomo-linoleate, mead acid, docosatrienoate), medium chain fatty acids (MCFAs) (e.g. heptanoate, cis-4-decenoate, 10-undecenoate, 5-dodecenoate etc.), fatty acids dicarboxylate (e.g. glutarate, 2-hydroxyglutarate, 2-hydroxyadipate, 3-hydroxyadipate, suberate, azelate, sebacate, dodecadienoate, dodecanedioate, tetradecanedioate, hexadecanedioate, octadecenedioate, tetradecadienedioate, 3-carbodyy-4-methyl-5-propyl-2-furanpropanoate, 3-carboxy-4-methyl-5-pentyl-2-furanpropionate etc.), amino fatty acids (e.g. 2-aminoheptanoate, 2-aminooctanoate, n-acetyl-2-aminooctanoate etc.), acyl glycine (e.g. isocaproylglycine, valerylglycine, hexanoylglycine, 4-methylhexanoylglycine, trans-2-hexenoylglycine, n-octanoylglycine, 2-butenoylglycine, 3-hydroxybutyroylglycine etc.) and carnitines (e.g. acetylcarnitine, (R)-3-hydroxybutyrrylcarnitine, hexanoylcarnitine, octanoylcarnitine, decanoylcarnitine, 5-dodecenoylcarnitine, cis-4-decenoylcarnitine, laurylcarnitine, myristoylcarnitine, palmitoylcarnitine palmitoleoylcarnitine, stearoylcarnitine, linoleoylcarnitine, linolenoylcarnitine, 3-hydroxyoleoylcarnitine, oleoylcarnitine, myristoleoylcarnitine, adipoylcarnitine, octadecenedioylcarnitine, arachidoylcarnitine, arachidonoylcarnitine, behenoylcarnitine, dihomo-linolenoylcarnitine, dihomo-linoleoylcarnitine, eicosenoylcanitine, docosahexaenoylcarnitine, lignoceroylcarnitine, nervonoylcarnitine, margaroylcarnitine, pentadecanoylcarnitine, 3-hydroxypalmitoylcarnitine, deoxycanitine, carnitine etc.) and beta-hydroxybutyrate. The redox potential is a robust biomarker to assess the safety and efficacy of MOEF and/or MNPMFs. The redox potential is calculated by the Nernst equation (Eo−RT/nF ln [reduced]2/[oxidized]) to yield a half-cell reduction potential (Eh) for the couple, where Eo is the standard half-cell reduction potential for the redox couple, R is the gas constant, T is the absolute temperature, n is 2 for the number of electrons transferred, and F is Faraday's constant. Schafer, F. Q. & Buettner, G. R. Redox environment of the cell as viewed through the redox state of the glutathione disulfide/glutathione couple. *Free Radical Biology and Medicine* 30, 1191-1212 (2001).

Metabolism, including both catabolic and anabolic pathways, is an optimally synchronized set of oxidation and reduction reactions (redox). Metabolism both produces ROS/RNS and is regulated by direct changes in the levels of ROS/RNS or indirectly, by activation of protein signaling via ROS/RNS or other induced secondary messengers. The regulation of ROS/RNS production is tightly controlled via a pro-oxidant-antioxidant system. Likewise, the inflammatory response used by immune cells leverages the same metabolic pathways to produce ROS/RNS to defend against pathogens and exogenous toxins and resets to basal levels via redox regulation through the tightly controlled pro-oxidant-antioxidant system. Aberrations in redox regulation and the nutrients supplied to immune cells can lead to disease states due to chronic systemic inflammation. Therefore, since MNPEFs and MNPMFs modulate redox, MNPEFs and MNPMFs may also be effective in treating inflammatory disease including infectious disease.

As a result of metabolism and the regulation of redox, these biomarkers can be detected in a variety of tissues, extracellular spaces and bodily fluids including but not limited to whole blood, plasma, serum, red blood cells, tears, urine, stool, cerebrospinal fluid, lymphatic fluid etc. These biomarkers are to be measured in subjects receiving treatment and compared to control samples which can be classified as the same subject before receiving treatment (paired sample) or an independent group of subjects that are matched to the subject receiving treatment in age, sex, disease type (e.g. type 2 diabetes, cancer, obesity, chronic kidney disease, Alzheimer's disease, depression, opioid addiction) that have not received treatment (independent sample) or a historical control (independent but retrospective sample). The above biomarkers of MOEF and MNPMFs may be used to determine treatment efficacy and safety in a wide range of metabolic and redox-related diseases and conditions such as type 2 diabetes, type 1 diabetes, cancer (e.g. liver, cancer, pancreatic cancer, bladder cancer, stomach cancer, colon cancer, breast cancer, prostate cancer, lung cancer, brain cancer, melanoma, lymphoma, sarcoma or leukemia), obesity, steatosis, glaucoma, retinopathy, aging, Alzheimer's disease, Parkinson's disease, Multiple Sclerosis, depression, Schizophrenia, addiction (e.g. alcoholism, opiate addiction etc.), inflammatory disease (e.g. gout, hepatitis (viral and NAFLD induced), Crohn's disease, celiac disease, ulcerative colitis, glomerulonephritis, lupus, rheumatoid arthritis, osteoarthritis, ankylosing spondylitis, myositis, amyloidosis, asthma, chronic obstructive pulmonary disease, atopic dermatitis, psoriasis, atherosclerosis, reperfusion injury, transplant rejection, and autoimmune diseases), and infectious disease.

Figure 19:
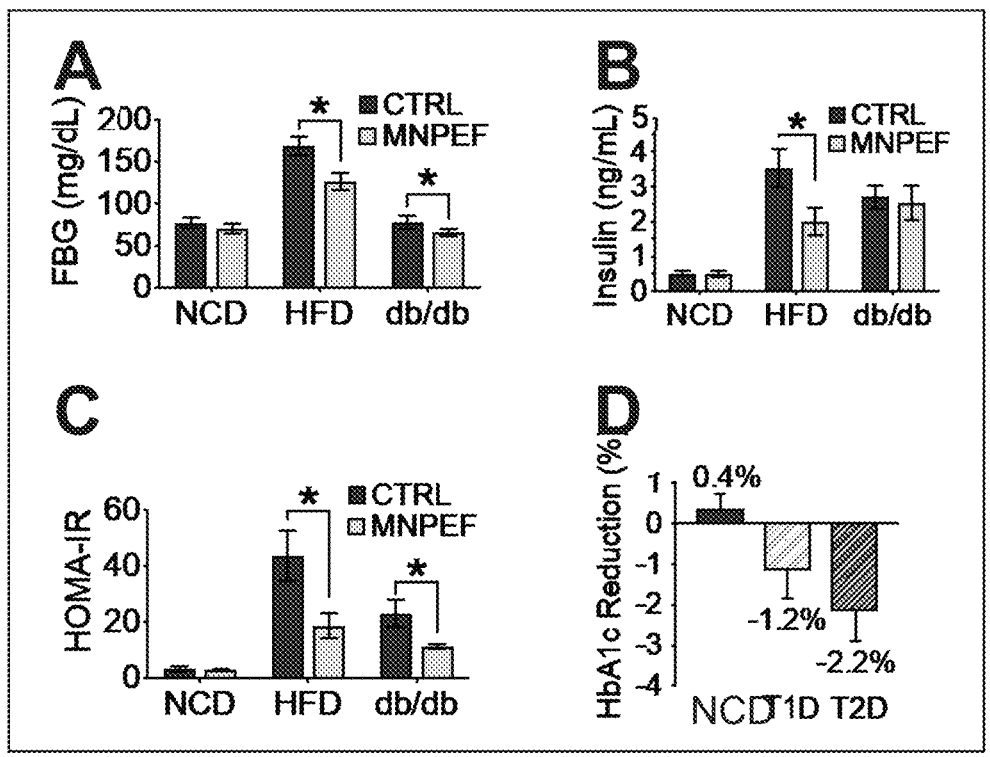
FIG. 19 shows that treatment with MNPEF reduces fasting blood glucose (FBG) in two different models of type 2 diabetes (T2D), does not increase levels of insulin which is consistent with an insulin-sensitizing effect, reduces HOMA-IR a measurement of insulin resistance, and reduces HbA1c in both type 1 diabetes (T1D) and type 2 diabetes (T2D).
Figure 20:
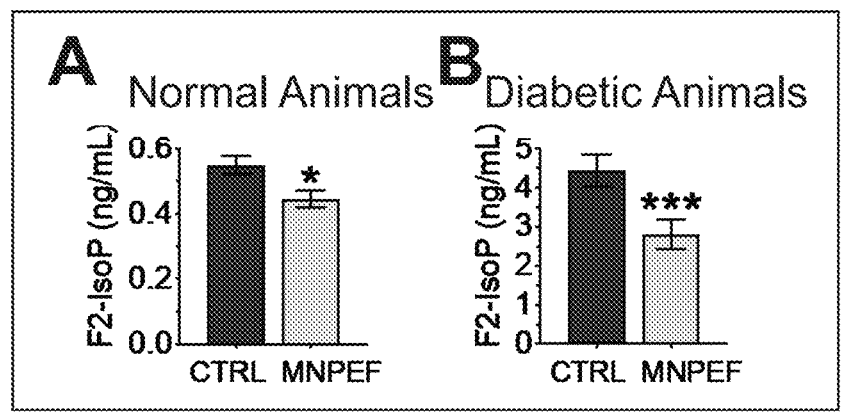
FIG. 20 shows a positive treatment effect in normal healthy and diabetic animal models is correlated with significant reductions in circulating levels of F2-isoprostanes.
Figure 21:
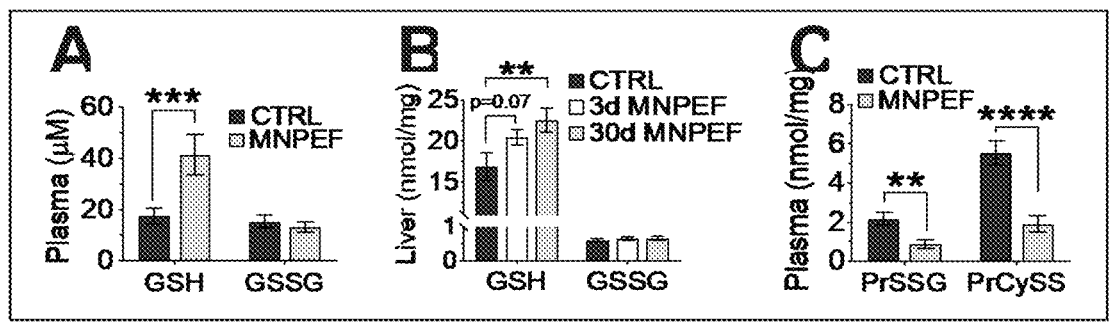
FIG. 21 shows significant increases in GSH in plasma and liver are observed in diabetic animal models upon treatment with MNPEFs and significant reductions in glutathionylation and cysteinylation occur with MNPEFs treatment for 3 days in diabetic animal models
Figure 22:
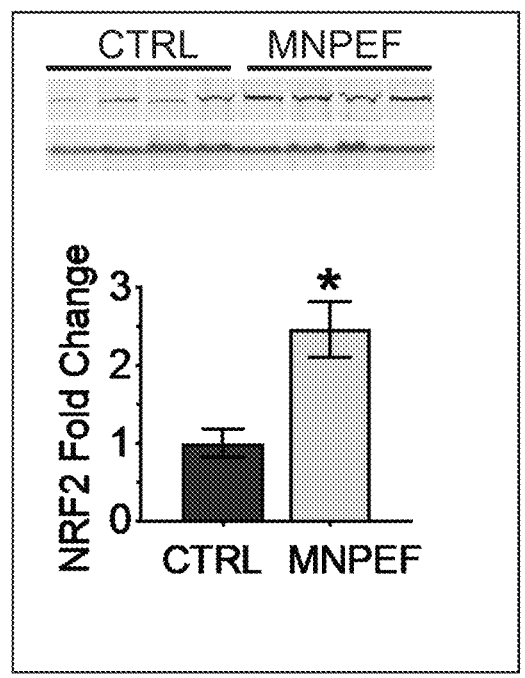
FIG. 22 shows that MNPEFs treatment for 3 days increases expression of NRF2 protein, a master regulator of antioxidant production, which will lead to a redox environment that is significantly more reducing than in untreated diabetic animals.
Figure 23A:
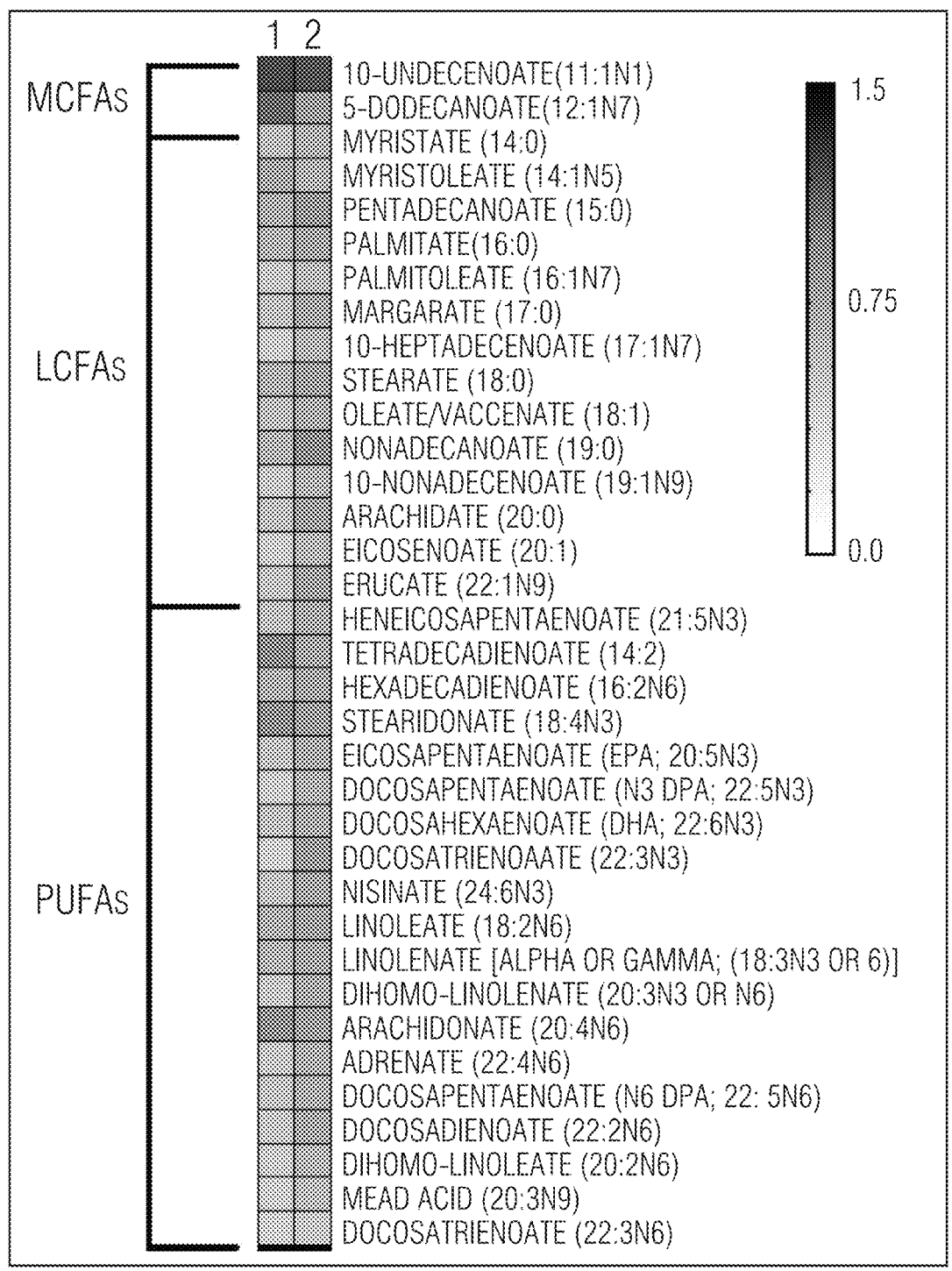
Figure 23B:
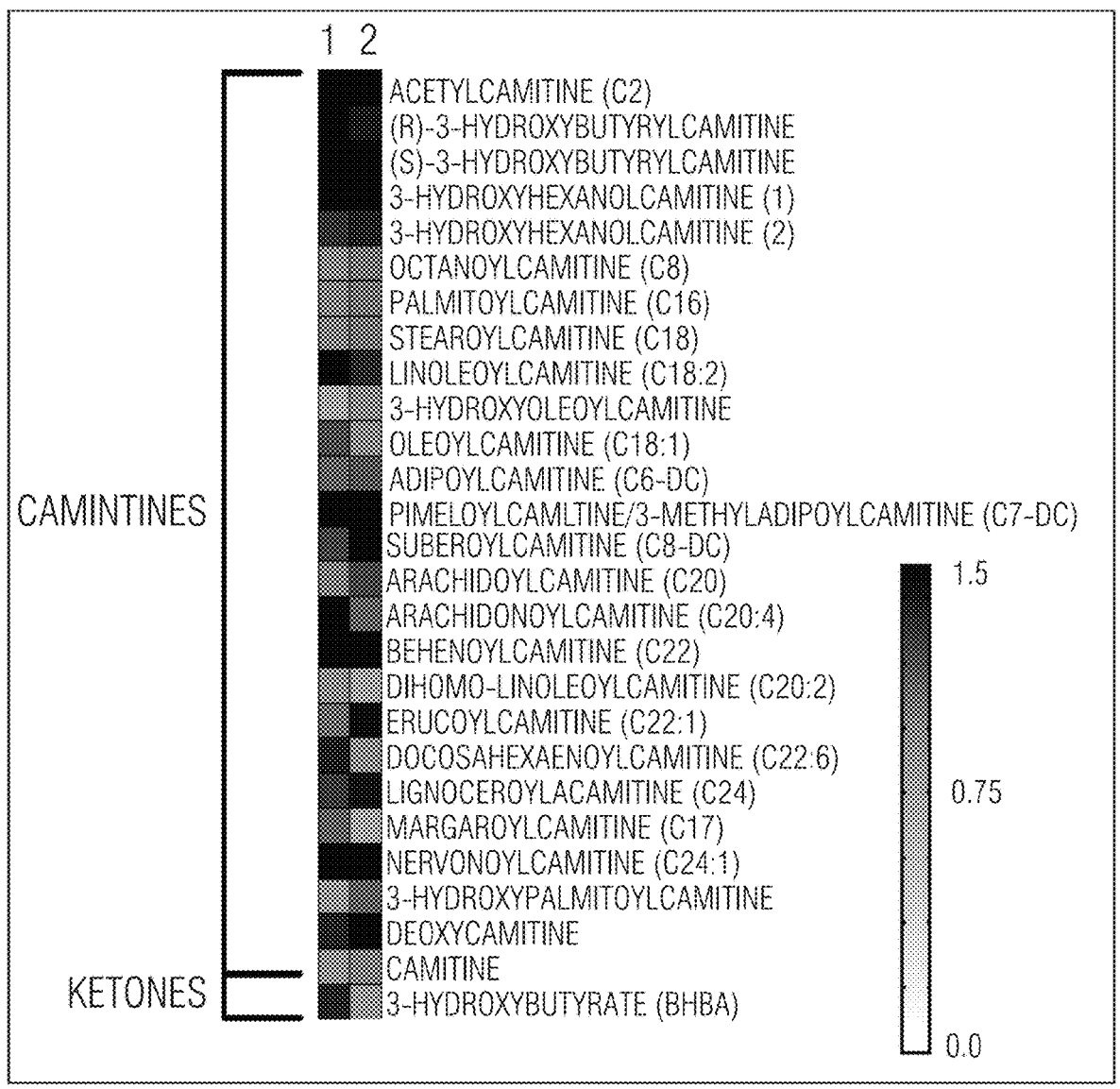
Figure 24A:
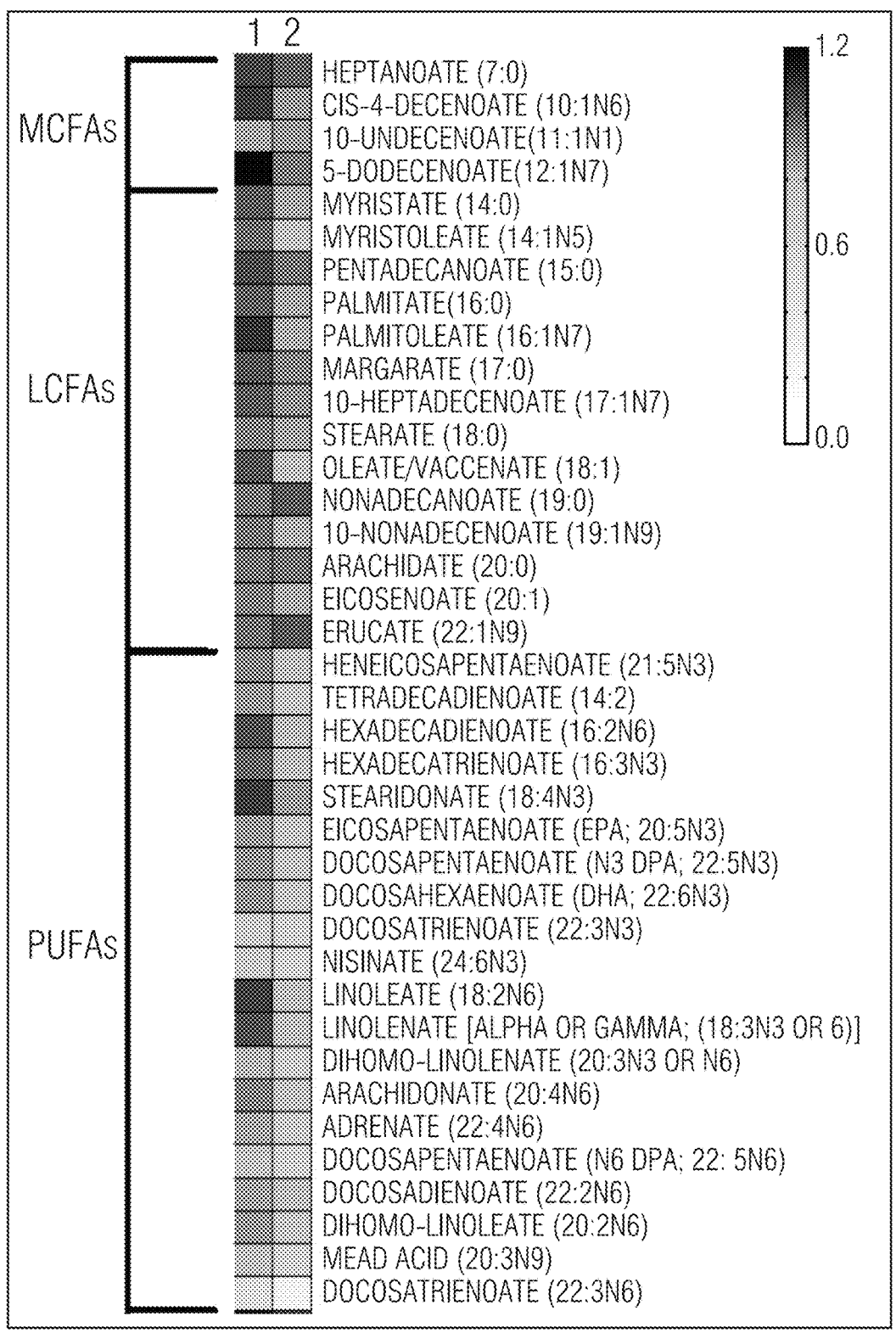
Figure 24B:
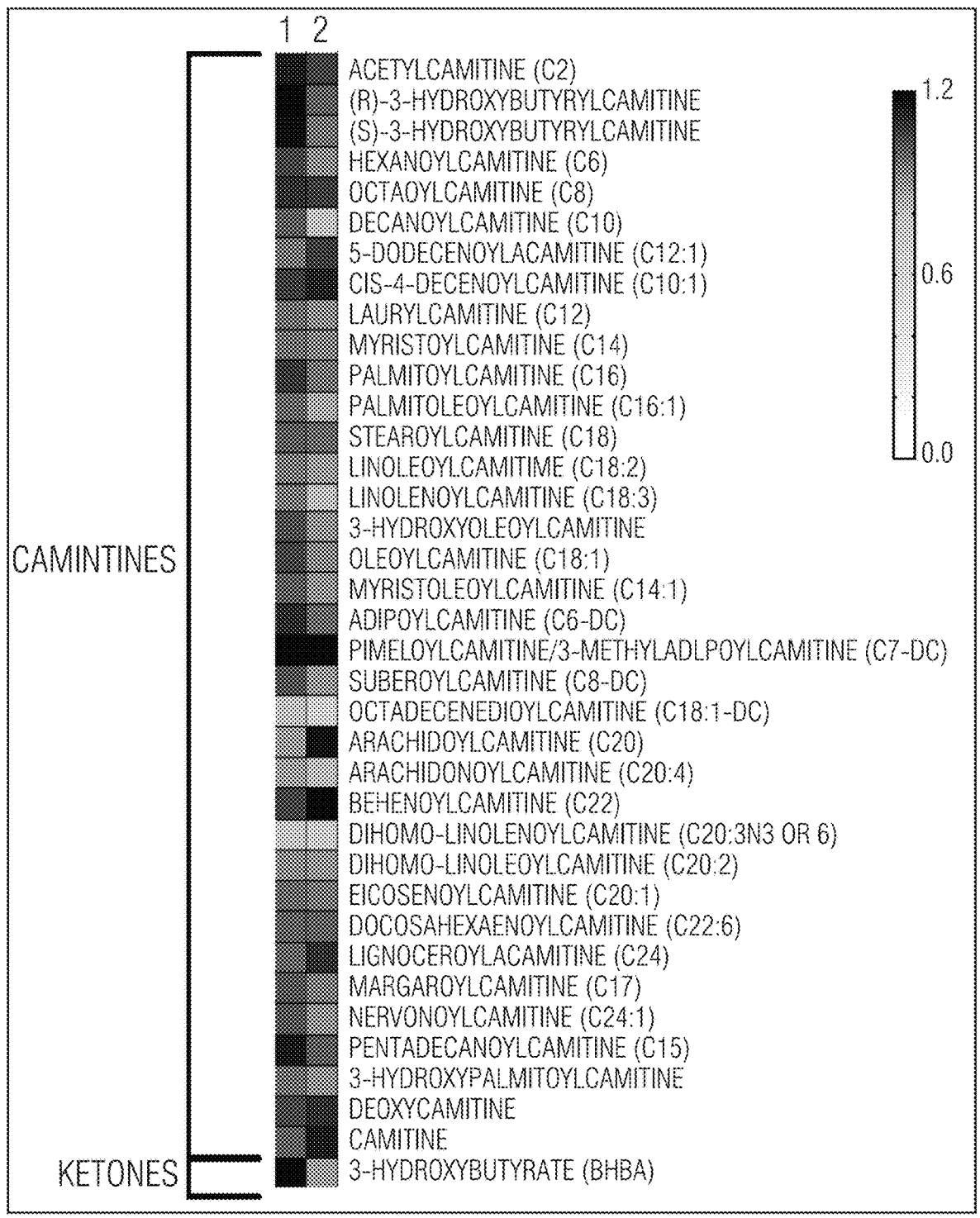

FIG. 19 shows that treatment with MNPEF reduces fasting blood glucose (FBG) in two different models of type 2 diabetes (T2D) (Graph A), does not increase levels of insulin which is consistent with an insulin-sensitizing effect (Graph B), reduces HOMA-IR a measurement of insulin resistance (Graph C), and reduces HbA1c in both type 1 diabetes (T1D) and type 2 diabetes (T2D) (Graph D). As shown in the data in FIG. 20, positive treatment effect in normal healthy (Graph A) and diabetic animal models (Graph B) is correlated with significant reductions in circulating levels of F2-isoprostanes. Significant increases in GSH in plasma and liver are observed in diabetic animal models upon treatment with MNPEFs (FIG. 21, Graphs A and B)). Significant reductions in glutathionylation and cysteinylation occur with MOEF treatment for 3 days in diabetic animal models (FIG. 21, Graph C). MOEF treatment for 3 days produced a redox environment that was significantly more reducing than in untreated diabetic animals (FIG. 22). Significant elevations in NRF2 nuclear localization was found after 3 days of MOEF treatment in diabetic animal models. When oxidative stress is reduced, levels of F2-isoprostanes are expected whereas increases in oxidative stress is associated with increases in F2-isoprostanes. Similarly, elevated levels of GSH are associated with lower oxidative stress.

Significant reductions in circulating (plasma) fatty acids including, MCFA, LCFA, PUFA, fatty acid dicarboxylates, acyl glycines, amino fatty acids, and significant increases in carnitines occur with 3 days of MOEF treatment in diabetic animal models (FIGS. 23A and 23B-24A and 24B).

Based on these data, one or more of the biomarkers listed above or various combinations of two or more of the biomarkers listed above may be used to determine safety and efficacy in various disease states listed above.

The above detailed description is intended to be illustrative, and not restrictive. The scope of the disclosure should, therefore, be determined with references to the appended claims, along with the full scope of equivalents to which such claims are entitled.

What is claimed is:

1. A method, comprising:
   identifying a subject having metabolic dysfunction or aberrant reactive oxygen species, reactive nitrogen species or oxidative stress;
   delivering a therapy to the subject to treat the metabolic dysfunction or the aberrant reactive oxygen species, reactive nitrogen species or oxidative stress by delivering energy to tissue, wherein delivering energy to the tissue includes:
   providing at least one magnetic field in a first direction to the tissue and in a second direction to the tissue using at least one magnetic field system including at least one magnetic field source to produce the at least one magnetic field, wherein the magnetic field produced by the magnetic field source includes a magnetic field produced by at least one of a permanent magnet, a temporary magnet or electric current flow through a conductor, wherein the second direction is non-parallel to the first direction.

2. The method of claim 1, further comprising providing an electric field to the tissue in a third direction non-parallel to both the first direction and the second direction using an electric field system including at least one electric field energy source to produce the electric field, wherein the electric field source and the at least one magnetic field source are different sources, and the at least one electric field energy source includes one or more of at least one a voltage source or at least one a current source electrically connected to at least one electrode to deliver the electric field in the third direction.

3. The method of claim 2, further comprising using a controller to control timing for the magnetic field in the first direction and in the second direction and to control timing for the electric field in the third direction independent from the timing for the magnetic field.

4. The method of claim 1, wherein the therapy is delivered for metabolic dysfunction, and the metabolic dysfunction includes abnormal glucose metabolism.

5. A method, comprising:
   identifying a mammal having a disease associated with metabolic dysfunction or aberrant reactive oxygen species, reactive nitrogen species or oxidative stress; and preventing, inhibiting or treating one or more symptoms of the disease by applying to one or more organs or tissues of the mammal at least one magnetic field in a first direction and a second direction, wherein the at least one magnetic field is provided by a system that includes at least one magnetic field source that includes at least one permanent magnet, a temporary magnet or electric current flow through a conductor to produce the at least one magnetic field, wherein the second direction is non-parallel to the first direction, effective to prevent, inhibit or treat the one or more symptoms of the disease in the mammal associated with aberrant reactive oxygen species, reactive nitrogen species or oxidative stress.

6. The method of claim 5, further comprising applying to the one or more organs or tissues of the mammal an electric field in a third direction non-parallel to both the first direction and the second direction using an electric field system including at least one electric field energy source to produce the electric field, wherein the electric field source and the at least one magnetic field source are different sources, and the at least one electric field energy source includes one or more of at least one a voltage source or at least one a current source electrically connected to at least one electrode to deliver the electric field in the third direction.

7. The method of claim 6, further comprising using a controller to control timing for the magnetic field in the first direction and in the second direction and to control timing for the electric field in the third direction independent from the timing for the magnetic field.

8. The method of claim 5, wherein the disease is associated with metabolic dysfunction, and the metabolic dysfunction includes abnormal glucose metabolism.

* * * * *